(12) United States Patent
MacLachlan et al.

(10) Patent No.: US 8,227,443 B2
(45) Date of Patent: Jul. 24, 2012

(54) SILENCING OF CSN5 GENE EXPRESSION USING INTERFERING RNA

(75) Inventors: Ian MacLachlan, Mission (CA); Adam Judge, Vancouver (CA); Snorri S. Thorgeirsson, Bethesda, MD (US); Yun-Han Lee, Rockville, MD (US)

(73) Assignees: Protiva Biotherapeutics, Inc., Burnaby, BC (CA); The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 12/903,558

(22) Filed: Oct. 13, 2010

(65) Prior Publication Data

US 2011/0178155 A1   Jul. 21, 2011

Related U.S. Application Data

(63) Continuation of application No. PCT/US2009/040685, filed on Apr. 15, 2009.

(60) Provisional application No. 61/045,251, filed on Apr. 15, 2008.

(51) Int. Cl.
*A61K 31/70* (2006.01)
*C07H 21/02* (2006.01)
*C07H 21/04* (2006.01)
*C12Q 1/68* (2006.01)

(52) U.S. Cl. .............. 514/44 A; 536/23.1; 536/24.1; 536/24.5; 435/375; 435/377

(58) Field of Classification Search ............... None
See application file for complete search history.

(56) References Cited

U.S. PATENT DOCUMENTS

| 8,090,542 B2 * | 1/2012 | Khvorova et al. ............. 702/20 |
| 2005/0069918 A1 | 3/2005 | Claret |
| 2006/0111314 A1 | 5/2006 | Nakamura et al. |
| 2008/0113351 A1 * | 5/2008 | Naito et al. ................ 435/6 |

FOREIGN PATENT DOCUMENTS

WO   WO 2004/045543 A2   6/2004

OTHER PUBLICATIONS

Adler, A.S. et al., "CSN5 isopeptidase activity links C0P9 signalosome activation to breast cancer progression," Cancer Research, 68(2):506-515, 2008.
Adler, A.S. et al., "Genetic regulators of large-scale transcriptional signatures in cancer," Nature Genetics, 38(4):421-430, 2006.
Chamovitz, D.A. and Segal, D., "JAB1/CSN5 and the COP9 signalosome," EMBO Reports, 2(2):96-101, 2001.
Czauderna, F. et al., "Structural variations and stabilizing modifications of synthetic siRNAs in mammalian cells," Nucleic Acids Research, 31(11):2705-2716, 2003.
Database Registry [Online], Seq. ID No. 769938, Nov. 10, 2004, XP002545474, Database accession No. 778103-12-1, abstract.
Database Registry [Online], Seq. ID No. 769941, Nov. 10, 2004, XP002545473, Database accession No. 778103-15-4, abstract.
Database Registry [Online], Seq. ID No. 769949, Nov. 10, 2004, XP002545472, Database accession No. 778103-23-4, abstract.
Database Registry [Online], Sequences 769965, 769949, 769941, 769938, Seq. ID No. 769965, Nov. 10, 2004, XP002545471, Database accession No. 778103-39-2, abstract.
Fukumoto, A. et al., "Depletion of Jab1 inhibits proliferation of pancreatic cancer cell lines," FEBS Letters, 580(25):5836-5844, 2006.
Groisman, R. et al., "The ubiquitin ligase activity in the DDB2 and CSA complexes is differentially regulated by the COP9 signalosome in response to DNA damage," Cell, 113:357-367, 2003.
Hsu, M.C. et al., "Jab1 is over expressed in human breast cancer and is a downstream target for HER-2/neu," Modern Pathology, 21(5):609-616, 2008.
Judge, A.D. et al., "Design of Noninflammatory Synthetic siRNA Mediating Potent Gene Silencing in Vivo," Molecular Therapy, 13(3):494-505, 2006.
Kameda, K. et al., "CSN5/Jab1 inhibits cardiac L-type $Ca^{2+}$ channel activity through protein-protein interactions," Journal of Molecular and Cellular Cardiology, 40:562-569, 2006.
Kaposi-Novak, P. et al., "Central role of c-Myc during malignant conversion in human hepatocarcinogenesis," Cancer Research, 69(7):2775-82, 2009.
Kim, B.C. et al., "Jab1/CSN5, a component of the COP9 signalosome, regulates transforming growth factor β signaling by binding to smad7 and promoting its degradation," Molecular and Cellular Biology, 24(6):2251-2262, 2004.
Lee, E.W. et al., "Jab1 as a mediator of nuclear export and cytoplasmic degradation of p53," Mol. Cells, 22(2):133-140, 2006.
Lee, J.S. et al., "Classification and prediction of survival in hepatocellular carcinoma by gene expression profiling," Hepatology, 40:667-676, 2004.
Lee, Y.H. et al., "Molecular targeting of CSN5, a negative regulator of p53 and p27, for treatment of human HCC," AACR Meeting Abstracts, Apr. 2008, 2008:5837.
Patil, M.A. et al., "Array-based comparative genomic hybridization reveals recurrent chromosomal aberrations and Jab1 as a potential target for 8q gain in hepatocellular carcinoma," Carcinogenesis, 26(12):2050-57, 2005.
Richardson, K.S. and Zundel, W., "The emerging role of the COP9 signalosome in cancer," Mol. Cancer Res., 3(12):645-653, 2005.
Yun, J. et al., "Interaction between glucose-regulated destruction domain of DNA topoisomerase IIα and MPN domain of jab1/CSN5," Journal of Biological Chemistry, 279(30):31296-31303, 2004.

* cited by examiner

*Primary Examiner* — Sean McGarry
(74) *Attorney, Agent, or Firm* — Kilpatrick Townsend & Stockton LLP

(57) ABSTRACT

The present invention provides compositions comprising nucleic acids that target CSN5 gene expression and methods of using such compositions to silence CSN5 gene expression. More particularly, the present invention provides unmodified and chemically modified interfering RNA molecules which silence CSN5 gene expression and methods of use thereof, e.g., for treating cell proliferative disorders such as cancer. The present invention also provides nucleic acid-lipid particles that target CSN5 gene expression comprising an interfering RNA molecule, a cationic lipid, a non-cationic lipid, and optionally a conjugated lipid that inhibits aggregation of particles.

20 Claims, 13 Drawing Sheets

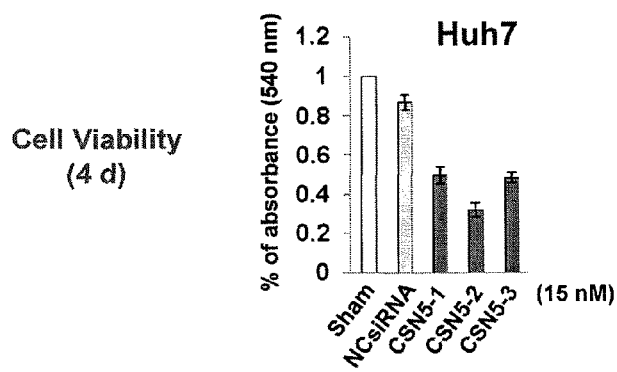
FIG. 4A Huh7
FIG. 4B HepG2
Cell Viability (4 d)
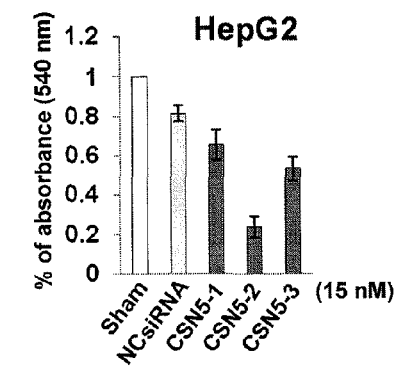
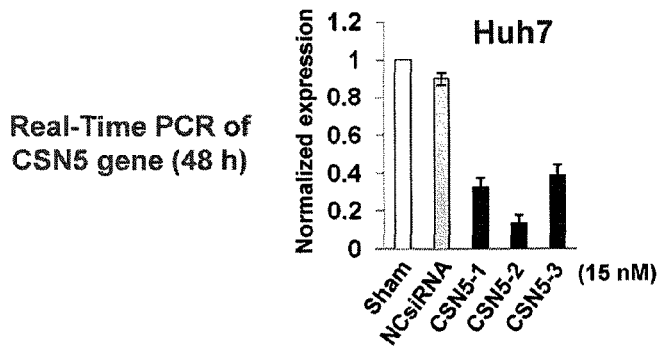
FIG. 4C Huh7
FIG. 4D HepG2
Real-Time PCR of CSN5 gene (48 h)
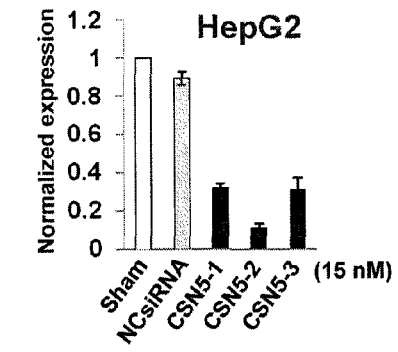

FACS Analysis (48h)
Huh7
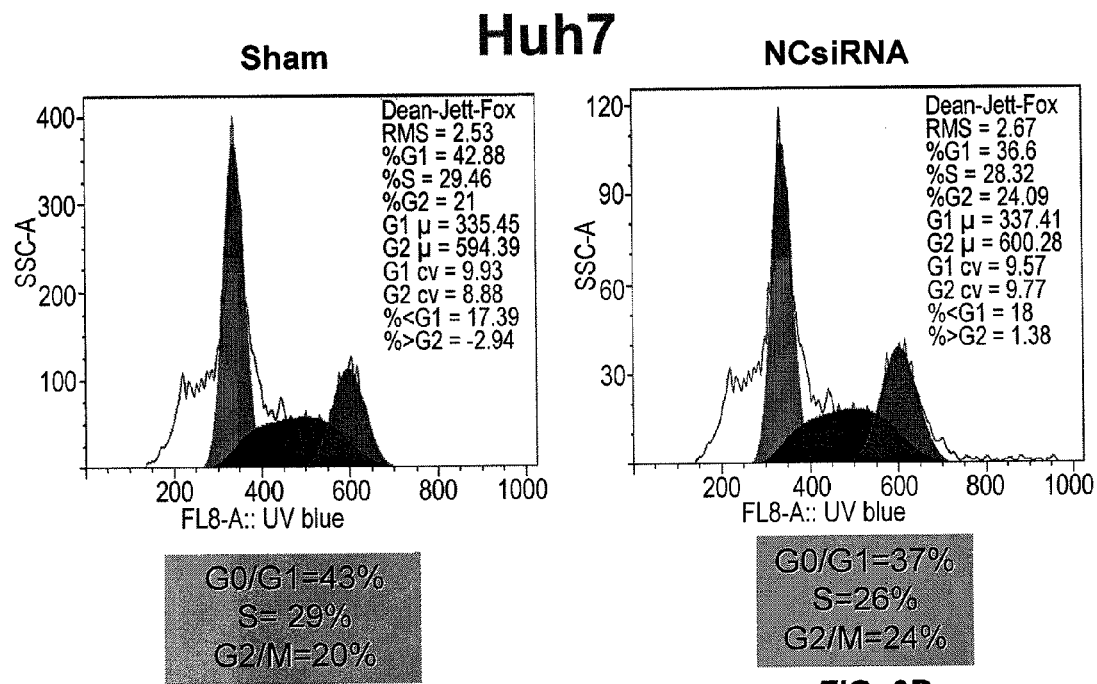
*FIG. 6A*
*FIG. 6B*
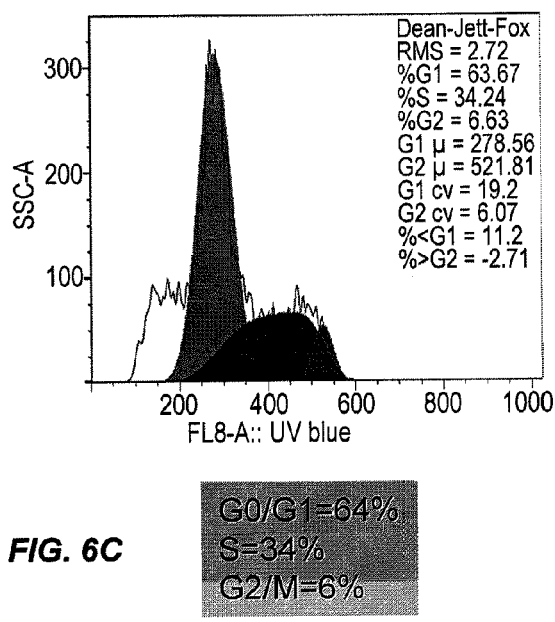
*FIG. 6C*

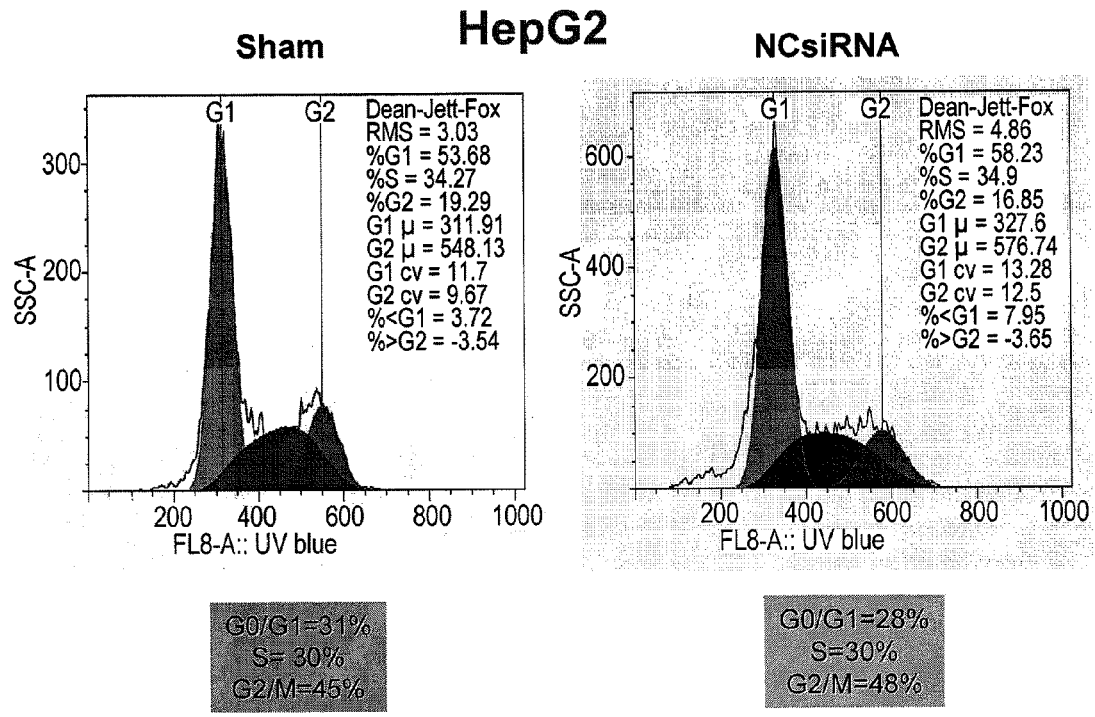
*FIG. 6D*                    *FIG. 6E*
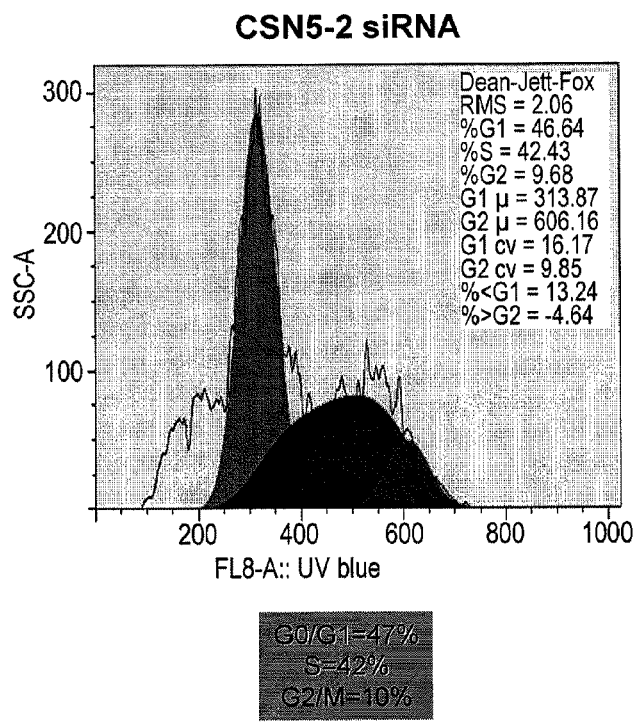
*FIG. 6F*

FACS analysis with Hoechst 33342 dye staining (48 h)
Huh7
NCsiRNA

CSN5-2 siRNA

Stable expression of luciferase in Huh7 cells

Transplantation of Huh7-1H6-luc+ cells

500,000 cells were transplanted into the spleen of immunodeficient SCID/BEIGE mice Tumor bioluminescence (mean ± SD)

SEQUENCE LISTING

<160> NUMBER OF SEQ ID NOS: 38

<210> SEQ ID NO 1

```
<211> LENGTH: 19
<212> TYPE: RNA
<213> ORGANISM: Artificial Sequence
<220> FEATURE:
<223> OTHER INFORMATION: synthetic siRNA CSN5-478 (CSN5-1) target or
      sense strand

<400> SEQUENCE: 1
ccauuacuuu aaguacugc                                                  19

<210> SEQ ID NO 2
<211> LENGTH: 19
<212> TYPE: RNA
<213> ORGANISM: Artificial Sequence
<220> FEATURE:
<223> OTHER INFORMATION: synthetic siRNA CSN5-478 (CSN5-1) antisense
      strand

<400> SEQUENCE: 2
gcaguacuua aaguaaugg                                                  19

<210> SEQ ID NO 3
<211> LENGTH: 19
<212> TYPE: RNA
<213> ORGANISM: Artificial Sequence
<220> FEATURE:
<223> OTHER INFORMATION: synthetic siRNA CSN5-472 (CSN5-2) target or
      sense strand

<400> SEQUENCE: 3
ggaucaccau uacuuuaag                                                  19

<210> SEQ ID NO 4
<211> LENGTH: 19
<212> TYPE: RNA
<213> ORGANISM: Artificial Sequence
<220> FEATURE:
<223> OTHER INFORMATION: synthetic siRNA CSN5-472 (CSN5-2) antisense
      strand

<400> SEQUENCE: 4
cuuaaaguaa uggugaucc                                                  19

<210> SEQ ID NO 5
<211> LENGTH: 19
<212> TYPE: RNA
<213> ORGANISM: Artificial Sequence
<220> FEATURE:
<223> OTHER INFORMATION: synthetic siRNA CSN5-1210 (CSN5-3) target or
      sense strand

<400> SEQUENCE: 5
ccgaaaauca gaagacaaa                                                  19

<210> SEQ ID NO 6
<211> LENGTH: 19
<212> TYPE: RNA
<213> ORGANISM: Artificial Sequence
<220> FEATURE:
<223> OTHER INFORMATION: synthetic siRNA CSN5-1210 (CSN5-3) antisense
      strand

<400> SEQUENCE: 6
uuugucuucu gauuuucgg                                                  19

<210> SEQ ID NO 7
<211> LENGTH: 19
<212> TYPE: RNA
```

```
<213> ORGANISM: Artificial Sequence
<220> FEATURE:
<223> OTHER INFORMATION: synthetic siRNA CSN5-215 target or sense strand

<400> SEQUENCE: 7
gagucuaggu aagaguuug                                                    19

<210> SEQ ID NO 8
<211> LENGTH: 19
<212> TYPE: RNA
<213> ORGANISM: Artificial Sequence
<220> FEATURE:
<223> OTHER INFORMATION: synthetic siRNA CSN5-215 antisense strand

<400> SEQUENCE: 8
caaacucuua ccuagacuc                                                    19

<210> SEQ ID NO 9
<211> LENGTH: 19
<212> TYPE: RNA
<213> ORGANISM: Artificial Sequence
<220> FEATURE:
<223> OTHER INFORMATION: synthetic siRNA CSN5-1284 target or sense
      strand

<400> SEQUENCE: 9
ugaugucuca gguuauuaa                                                    19

<210> SEQ ID NO 10
<211> LENGTH: 19
<212> TYPE: RNA
<213> ORGANISM: Artificial Sequence
<220> FEATURE:
<223> OTHER INFORMATION: synthetic siRNA CSN5-1284 antisense strand

<400> SEQUENCE: 10
uuaauaaccu gagacauca                                                    19

<210> SEQ ID NO 11
<211> LENGTH: 19
<212> TYPE: RNA
<213> ORGANISM: Artificial Sequence
<220> FEATURE:
<223> OTHER INFORMATION: synthetic siRNA CSN5-655 target or sense strand

<400> SEQUENCE: 11
ugcucaggcu gcugcauau                                                    19

<210> SEQ ID NO 12
<211> LENGTH: 19
<212> TYPE: RNA
<213> ORGANISM: Artificial Sequence
<220> FEATURE:
<223> OTHER INFORMATION: synthetic siRNA CSN5-655 antisense strand

<400> SEQUENCE: 12
auaugcagca gccugagca                                                    19

<210> SEQ ID NO 13
<211> LENGTH: 19
<212> TYPE: RNA
<213> ORGANISM: Artificial Sequence
<220> FEATURE:
<223> OTHER INFORMATION: synthetic siRNA CSN5-904 target or sense strand

<400> SEQUENCE: 13
gggcuacaaa ccuccugau                                                    19
```

<210> SEQ ID NO 14
<211> LENGTH: 19
<212> TYPE: RNA
<213> ORGANISM: Artificial Sequence
<220> FEATURE:
<223> OTHER INFORMATION: synthetic siRNA CSN5-904 antisense strand

<400> SEQUENCE: 14
aucaggaggu uuguagccc                                                19

<210> SEQ ID NO 15
<211> LENGTH: 19
<212> TYPE: RNA
<213> ORGANISM: Artificial Sequence
<220> FEATURE:
<223> OTHER INFORMATION: synthetic siRNA CSN5-940 target or sense strand

<400> SEQUENCE: 15
ccagacuauu ccacuuaau                                                19

<210> SEQ ID NO 16
<211> LENGTH: 19
<212> TYPE: RNA
<213> ORGANISM: Artificial Sequence
<220> FEATURE:
<223> OTHER INFORMATION: synthetic siRNA CSN5-940 antisense strand

<400> SEQUENCE: 16
auuaagugga auagucugg                                                19

<210> SEQ ID NO 17
<211> LENGTH: 19
<212> TYPE: RNA
<213> ORGANISM: Artificial Sequence
<220> FEATURE:
<223> OTHER INFORMATION: synthetic siRNA CSN5-997 target or sense strand

<400> SEQUENCE: 17
ugccuuagaa gucucauau                                                19

<210> SEQ ID NO 18
<211> LENGTH: 19
<212> TYPE: RNA
<213> ORGANISM: Artificial Sequence
<220> FEATURE:
<223> OTHER INFORMATION: synthetic siRNA CSN5-997 antisense strand

<400> SEQUENCE: 18
auaugagacu ucuaaggca                                                19

<210> SEQ ID NO 19
<211> LENGTH: 19
<212> TYPE: RNA
<213> ORGANISM: Artificial Sequence
<220> FEATURE:
<223> OTHER INFORMATION: synthetic siRNA CSN5-1022 target or sense
      strand

<400> SEQUENCE: 19
uccucuuugg aucgcaaau                                                19

<210> SEQ ID NO 20
<211> LENGTH: 19
<212> TYPE: RNA
<213> ORGANISM: Artificial Sequence
<220> FEATURE:

<223> OTHER INFORMATION: synthetic siRNA CSN5-1022 antisense strand

<400> SEQUENCE: 20
auuugcgauc caaagagga                                                                19

<210> SEQ ID NO 21
<211> LENGTH: 19
<212> TYPE: RNA
<213> ORGANISM: Artificial Sequence
<220> FEATURE:
<223> OTHER INFORMATION: synthetic siRNA CSN5-471 target or sense strand

<400> SEQUENCE: 21
aggaucacca uuacuuuaa                                                                19

<210> SEQ ID NO 22
<211> LENGTH: 19
<212> TYPE: RNA
<213> ORGANISM: Artificial Sequence
<220> FEATURE:
<223> OTHER INFORMATION: synthetic siRNA CSN5-471 antisense strand

<400> SEQUENCE: 22
uuaaaguaau ggugauccu                                                                19

<210> SEQ ID NO 23
<211> LENGTH: 19
<212> TYPE: RNA
<213> ORGANISM: Artificial Sequence
<220> FEATURE:
<223> OTHER INFORMATION: synthetic siRNA CSN5-1045 target or sense
      strand

<400> SEQUENCE: 23
ugagcuguug uggaauaaa                                                                19

<210> SEQ ID NO 24
<211> LENGTH: 19
<212> TYPE: RNA
<213> ORGANISM: Artificial Sequence
<220> FEATURE:
<223> OTHER INFORMATION: synthetic siRNA CSN5-1045 antisense strand

<400> SEQUENCE: 24
uuuauuccac aacagcuca                                                                19

<210> SEQ ID NO 25
<211> LENGTH: 19
<212> TYPE: RNA
<213> ORGANISM: Artificial Sequence
<220> FEATURE:
<223> OTHER INFORMATION: synthetic siRNA CSN5-1437 target or sense
      strand

<400> SEQUENCE: 25
gcucugaagu guccuaaau                                                                19

<210> SEQ ID NO 26
<211> LENGTH: 19
<212> TYPE: RNA
<213> ORGANISM: Artificial Sequence
<220> FEATURE:
<223> OTHER INFORMATION: synthetic siRNA CSN5-1437 antisense strand

<400> SEQUENCE: 26
auuuaggaca cuucagagc                                                                19

<210> SEQ ID NO 27
<211> LENGTH: 19
<212> TYPE: RNA
<213> ORGANISM: Artificial Sequence
<220> FEATURE:
<223> OTHER INFORMATION: synthetic siRNA CSN5-3/6, CSN5-3/7, CSN5-3/8
      and CSN5-3/9 target or sense strand
<220> FEATURE:
<221> NAME/KEY: modified_base
<222> LOCATION: (4)...(16)
<223> OTHER INFORMATION: n = um

<400> SEQUENCE: 27
ggancaccau nacnunaag                                                19

<210> SEQ ID NO 28
<211> LENGTH: 19
<212> TYPE: RNA
<213> ORGANISM: Artificial Sequence
<220> FEATURE:
<223> OTHER INFORMATION: synthetic siRNA CSN5-3/6, CSN5-4/6 and CSN5-5/6
      antisense strand
<220> FEATURE:
<221> NAME/KEY: modified_base
<222> LOCATION: (2)...(17)
<223> OTHER INFORMATION: n = um

<400> SEQUENCE: 28
cnuaaaguaa uggugancc                                                19

<210> SEQ ID NO 29
<211> LENGTH: 19
<212> TYPE: RNA
<213> ORGANISM: Artificial Sequence
<220> FEATURE:
<223> OTHER INFORMATION: synthetic siRNA CSN5-3/7, CSN5-4/7 and CSN5-5/7
      antisense strand
<220> FEATURE:
<221> NAME/KEY: modified_base
<222> LOCATION: (2)...(3)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 29
cnnaaaguaa ungugancc                                                19

<210> SEQ ID NO 30
<211> LENGTH: 19
<212> TYPE: RNA
<213> ORGANISM: Artificial Sequence
<220> FEATURE:
<223> OTHER INFORMATION: synthetic siRNA CSN5-3/8, CSN5-4/8 and CSN5-5/8
      antisense strand
<220> FEATURE:
<221> NAME/KEY: modified_base
<222> LOCATION: (7)...(15)
<223> OTHER INFORMATION: n = gm

<400> SEQUENCE: 30
cuuaaanuaa ugnunaucc                                                19

<210> SEQ ID NO 31
<211> LENGTH: 19
<212> TYPE: RNA

```
<213> ORGANISM: Artificial Sequence
<220> FEATURE:
<223> OTHER INFORMATION: synthetic siRNA CSN5-3/9, CSN5-4/9 and CSN5-5/9
      antisense strand
<220> FEATURE:
<221> NAME/KEY: modified_base
<222> LOCATION: (3)...(14)
<223> OTHER INFORMATION: n = um

<400> SEQUENCE: 31
cunaaaguaa uggngaucc                                                    19

<210> SEQ ID NO 32
<211> LENGTH: 19
<212> TYPE: RNA
<213> ORGANISM: Artificial Sequence
<220> FEATURE:
<223> OTHER INFORMATION: synthetic siRNA CSN5-4/6, CSN5-4/7, CSN5-4/8
      and CSN5-4/9 target or sense strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (19)...(19)
<223> OTHER INFORMATION: n = gm

<400> SEQUENCE: 32
ngaucaccau uacunuaan                                                    19

<210> SEQ ID NO 33
<211> LENGTH: 19
<212> TYPE: RNA
<213> ORGANISM: Artificial Sequence
<220> FEATURE:
<223> OTHER INFORMATION: synthetic siRNA CSN5-5/6, CSN5-5/7, CSN5-5/8
      and CSN5-5/9 target or sense strand
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (4)...(16)
<223> OTHER INFORMATION: n = um

<400> SEQUENCE: 33
gnancaccau uacunnaag                                                    19

<210> SEQ ID NO 34
<211> LENGTH: 1510
<212> TYPE: DNA
<213> ORGANISM: Homo sapiens
<220> FEATURE:
<223> OTHER INFORMATION: COP9 signalosome subunit 5 (CSN5), Jun
      activating binding protein (Jab1), COPS5, SGN5, MOV-34,
      MGC3149 cDNA
<220> FEATURE:
<221> NAME/KEY: CDS
<222> LOCATION: (332)...(1336)
<223> OTHER INFORMATION: CSN5

<400> SEQUENCE: 34
gactatacca ctcccatacc ctataacttt gtttgttcta tttcacacat ataatttttcc      60 gagacaagat gttctcattt aagcaacaag aagattcgtc tctcgctatt actgtaactg     120
ctgtttatat cgtcatgtcc cggaaaggtc cctgtcttcc ctgaatggtc tctaccaact     180
```

```
tcacctccgg ttctaggtgt catggctgcc ccaagagtct aggtaagagt ttgttcccgt      240
ggtgcggagg gtcaaggccc acacccggaa acctagcgag gtaaagttgc gtcttggttg      300
tagagacgac aacttctccg cttcctcggc gatggcggcg tccgggagcg gtatggccca      360
gaaaacctgg gaactggcca acaacatgca ggaagctcag agtatcgatg aaatctacaa      420
atacgacaag aaacagcagc aagaaatcct ggcggcgaag ccctggacta aggatcacca      480
ttactttaag tactgcaaaa tctcagcatt ggctctgctg aagatggtga tgcatgccag      540
atcgggaggc aacttggaag tgatgggtct gatgctagga aggtggatg gtgaaaccat       600 gatcattatg gacagttttg ctttgcctgt ggagggcact gaaacccgag taaatgctca      660
ggctgctgca tatgaataca tggctgcata catagaaaat gcaaacagg ttggccgcct       720 tgaaaatgca atcgggtggt atcatagcca ccctggctat ggctgctggc tttctgggat      780
tgatgttagt actcagatgc tcaatcagca gttccaggaa ccatttgtag cagtggtgat      840
tgatccaaca agaacaatat ccgcagggaa agtgaatctt ggcgccttta ggacataccc      900
aaagggctac aaacctcctg atgaaggacc ttctgagtac cagactattc cacttaataa      960
aatagaagat tttggtgtac actgcaaaca atattatgcc ttagaagtct catatttcaa     1020
atcctctttg gatcgcaaat tgcttgagct gttgtggaat aaatactggg tgaatacgtt     1080
gagttcttct agcttgctta ctaatgcaga ctataccact ggtcaggtct ttgatttgtc     1140
tgaaaagtta gagcagtcag aagcccagct gggacgaggg agtttcatgt tgggtttaga     1200
aacgcatgac cgaaaatcag aagacaaact tgccaaagct acaagagaca gctgtaaaac     1260
taccatagaa gctatccatg gattgatgtc tcaggttatt aaggataaac tgtttaatca     1320
aattaacatc tcttaaacag tctctgagaa gtactttacc tgaaagacag tatgagaaaa     1380
atattcaagt aacactttaa aaccagttac ccaaaatctg attagaagta taaggtgctc     1440
tgaagtgtcc taaatattaa tatcctgtaa taaagctctt taaaatgaaa aaaaaaaaa      1500 aaaaaaaaaa                                                            1510

<210> SEQ ID NO 35
<211> LENGTH: 21
<212> TYPE: DNA
<213> ORGANISM: Artificial Sequence
<220> FEATURE:
<223> OTHER INFORMATION: synthetic siRNA beta-galactosidase betagal478
      sense strand
<220> FEATURE:
<223> OTHER INFORMATION: Description of Combined DNA/RNA Molecule:
      synthetic siRNA beta-galactosidase betagal478 sense strand
<220> FEATURE:
<221> NAME/KEY: modified_base
<222> LOCATION: (1)...(14)
<223> OTHER INFORMATION: n = gm
<220> FEATURE:
<221> NAME/KEY: modified_base
<222> LOCATION: (20)...(21)
<223> OTHER INFORMATION: n = deoxythymidine

<400> SEQUENCE: 35
naagnccaga cncnaauuan n                                                 21

<210> SEQ ID NO 36
<211> LENGTH: 21
<212> TYPE: DNA
<213> ORGANISM: Artificial Sequence
<220> FEATURE:
<223> OTHER INFORMATION: synthetic siRNA beta-galactosidase betagal478
      antisense strand
<220> FEATURE:
```

```
<223> OTHER INFORMATION: Description of Combined DNA/RNA Molecule:
      synthetic siRNA beta-galactosidase betagal478 antisense strand
<220> FEATURE:
<221> NAME/KEY: modified_base
<222> LOCATION: (5)...(17)
<223> OTHER INFORMATION: n = um
<220> FEATURE:
<221> NAME/KEY: modified_base
<222> LOCATION: (20)...(21)
<223> OTHER INFORMATION: n = deoxythymidine

<400> SEQUENCE: 36
uaauncgcgn cuggccnucn n                                              21

<210> SEQ ID NO 37
<211> LENGTH: 20
<212> TYPE: DNA
<213> ORGANISM: Artificial Sequence
<220> FEATURE:
<223> OTHER INFORMATION: synthetic RT-PCR CSN5 cDNA amplification
      forward primer

<400> SEQUENCE: 37
tctgctgaag atggtgatgc                                                20

<210> SEQ ID NO 38
<211> LENGTH: 20
<212> TYPE: DNA
<213> ORGANISM: Artificial Sequence
<220> FEATURE:
<223> OTHER INFORMATION: synthetic RT-PCR CSN5 cDNA amplification
      reverse primer

<400> SEQUENCE: 38
gccaacctgt tttgcatttt                                                20
```

SILENCING OF CSN5 GENE EXPRESSION USING INTERFERING RNA

CROSS-REFERENCES TO RELATED APPLICATIONS

The present application is a continuation of PCT/US2009/40685, filed Apr. 15, 2009, which claims priority to U.S. Provisional Application No. 61/045,251, filed Apr. 15, 2008, the disclosures of which are herein incorporated by reference in their entirety for all purposes.

STATEMENT REGARDING FEDERALLY SPONSORED RESEARCH OR DEVELOPMENT

This invention was created, in part, in the performance of a Collaboration Agreement with the National Cancer Institute, National Institutes of Health, an agency of the United States Government. The Government of the United States has certain rights in the invention.

BACKGROUND OF THE INVENTION

Cell proliferation and programmed cell death play important roles in the growth and development of an organism. In proliferative diseases such as cancer, the processes of cell proliferation and/or programmed cell death are often perturbed. For example, a cancer cell may have unregulated cell division through either the overexpression of a positive regulator of the cell cycle or the loss of a negative regulator of the cell cycle, perhaps by mutation. Alternatively, a cancer cell may have lost the ability to undergo programmed cell death through the overexpression of a negative regulator of apoptosis. Therefore, there is a need to develop new therapeutic agents that will restore the processes of checkpoint control and programmed cell death to cancerous cells.

RNA interference (RNAi) is an evolutionarily conserved process in which recognition of double-stranded RNA (dsRNA) ultimately leads to posttranscriptional suppression of gene expression. This suppression is mediated by short dsRNA, also called small interfering RNA (siRNA), which induces specific degradation of mRNA through complementary base pairing. In several model systems, this natural response has been developed into a powerful tool for the investigation of gene function (see, e.g., Elbashir et al., *Genes Dev.*, 15:188-200 (2001); Hammond et al., *Nat. Rev. Genet.*, 2:110-119 (2001)). More recently, it was discovered that introducing synthetic 21-nucleotide dsRNA duplexes into mammalian cells could efficiently silence gene expression. Although the precise mechanism is still unclear, RNAi offers a new way to inactivate genes of interest. In particular, for the treatment of neoplastic disorders such as cancer, RNAi provides a potential new approach to modulate (e.g., reduce) the expression of certain genes, e.g., an anti-apoptotic molecule, a growth factor, a growth factor receptor, a mitotic spindle protein, a cell cycle protein, an angiogenic factor, an oncogene, an intracellular signal transducer, a molecular chaperone, and combinations thereof.

One such target is the Jun activating binding protein (Jab1), first identified by its interaction with the activation domain of c-Jun (Claret et al., *Nature*, 383:453-457 (1996)). Jab1 stabilizes complexes of the transcription factors c-Jun or JunD at their specific AP-1 transcription factor binding sites, increasing the specificity of target gene activation. A homologous protein was identified in *Arabidopsis* as a component of the COP9 signalosome (CSN) (Kwok et al., *Plant Cell.*, 10:1779-1790 (1998)), and subsequently termed COP9 signalosome subunit 5 (CSN5) (Deng et al., *Trends Genet.*, 16:202-203 (2000)). Jab1/CSN5, also known as COPS5, is an ~40 kDa soluble protein. Like other CSN subunits, Jab1/CSN5 is highly conserved between the Plant and Animal Kingdoms, with the homologous proteins from *Arabidopsis* and humans sharing >60% amino acid identity. Jab1/CSN5 contains an MPN (MPR1-PAD1-Nterm) domain in its N-terminus (Hofmann et al., *Trends Biochem. Sci.*, 23:204-205 (1998)). This domain is common to several of the subunits of the CSN, to the regulatory lid of the proteasome, and to the translation initiation factor eIF3, as well as being present in several unknown proteins (Glickman et al., *Cell*, 94:615-623 (1998); Hofmann et al., supra; Wei et al., *Curr. Biol.*, 8:919-922 (1998)).

Overexpression of Jab1/CSN5 has been reported in breast cancer, ovarian cancer, pancreatic cancer, embryonal rhabdomyosarcoma, and oral squamous cell carcinomas (Kouvaraki et al., *Cancer Res.*, 63:2977-2981 (2003); Sui et al., *Clin. Cancer Res.*, 7:4130-4135 (2001); Tsuchida et al., *Jpn. J. Cancer Res.*, 93:1000-1006 (2002); Fukumoto et al., *Oncol. Rep.*, 11:277-284 (2004); Shintani et al., *Oncology*, 65:355-362 (2003)). In addition, high expression of Jab1/CSN5 has been associated with low levels of p27 and poor prognosis, indicating that Jab1/CSN5 may play an important role in the progression of these tumor types. A recent microarray-based expression profiling study of early cirrhotic and dysplastic nodules during human carcinogenesis has identified that activation of the Myc transcription signature is indispensable for malignant conversion of pre-neoplastic lesions to hepatocellular carcinoma (HCC) (Lee et al., *Hepatology*, 40:667-676 (2004)). In fact, the presence of the Myc transcription signature significantly correlated with elevated expression of Jab1/CSN5.

Currently, there are no known therapeutic agents which effectively inhibit Jab1/CSN5 expression in vivo and investigative strategies aimed at modulating Jab1/CSN5 function have involved the use of RNAi in an in vitro cell culture system. For example, reduction of Jab1/CSN5 expression using siRNA resulted in a modest inhibition of Hep3B cell growth in an in vitro cell proliferation assay (Patil et al., *Carcinogenesis*, 26:2050-2057 (2005)). Kim et al. (*Mol. Cell. Biol.*, 24:2251-2262 (2004)) and U.S. Patent Publication No. 20050069918 also describe in vitro cell culture systems using Jab1/CSN5 siRNA. However, these strategies are untested as therapeutic protocols for the treatment of cancers such as HCC and consequently there remains a long-felt need for agents capable of effectively inhibiting Jab1/CSN5 function in vivo.

Thus, there is a need for compositions and methods for specifically modulating Jab1/CSN5 gene expression. The present invention addresses these and other needs.

BRIEF SUMMARY OF THE INVENTION

The present invention provides compositions comprising nucleic acids (e.g., interfering RNA such as siRNA, aiRNA, and miRNA) that target CSN5 gene expression and methods of using such compositions to silence CSN5 gene expression. More particularly, the present invention provides unmodified and chemically modified interfering RNA molecules which silence CSN5 gene expression and methods of use thereof, e.g., for treating cell proliferative disorders such as cancer (e.g., liver cancer).

In one aspect, the present invention provides an siRNA molecule comprising a double-stranded region of about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length), wherein the siRNA molecule is capable of silencing CSN5 gene expression.

The siRNA may comprise at least one or a cocktail (e.g., at least two, three, four, five, six, seven, eight, nine, ten, or more) of sequences that silence CSN5 gene expression. In some embodiments, the siRNA comprises at least one or a cocktail of the sequences set forth in Tables 1-2. The CSN5 siRNA can be an unmodified sequence or can contain modified nucleotides (e.g., comprising at least one 2'OMe-nucleotide and/or any other modified nucleotides described herein). In certain preferred embodiments, a modified CSN5 siRNA sequence is less immunostimulatory than a corresponding unmodified siRNA sequence. In certain other preferred embodiments, the siRNA comprises or consists of the CSN5-2 siRNA sequence or a chemically modified version thereof such as CSN5-3/8.

In some embodiments, the siRNA further comprises a carrier system, e.g., to deliver the siRNA into a cell of a mammal. Examples of carrier systems suitable for use in the present invention include, but are not limited to, nucleic acid-lipid particles, liposomes, micelles, virosomes, nucleic acid complexes, and mixtures thereof.

In another aspect, the present invention provides a pharmaceutical composition comprising an siRNA described herein and a pharmaceutically acceptable carrier.

The present invention also provides serum-stable nucleic acid-lipid particles (e.g., SNALP) comprising an siRNA molecule described herein, a cationic lipid, and a non-cationic lipid, which can further comprise a conjugated lipid that inhibits aggregation of particles.

In preferred embodiments, the siRNA is fully encapsulated within the lipid portion of the nucleic acid-lipid particle such that the siRNA is resistant in aqueous solution to nuclease degradation. In other preferred embodiments, the particles are substantially non-toxic to mammals such as humans.

In certain aspects, the present invention provides nucleic acid-lipid particles (e.g., SNALP) comprising: (a) one or more siRNA molecules capable of silencing CSN5 gene expression; (b) one or more cationic lipids comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In some embodiments, the nucleic acid-lipid particle comprises: (a) an siRNA that silences CSN5 gene expression; (b) a cationic lipid comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:62" formulation.

In other embodiments, the nucleic acid-lipid particle comprises: (a) an siRNA that silences CSN5 gene expression; (b) a cationic lipid comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:57" formulation.

In additional embodiments, the nucleic acid-lipid particle comprises: (a) an siRNA that silences CSN5 gene expression; (b) a cationic lipid comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. This embodiment of nucleic acid-lipid particle is generally referred to herein as the "2:40" formulation.

In another aspect, the present invention provides pharmaceutical compositions comprising a nucleic acid-lipid particle described herein and a pharmaceutically acceptable carrier.

The present invention further provides methods of silencing CSN5 gene expression by delivering and/or administering one or more of the siRNA molecules described herein (e.g., encapsulated within nucleic acid-lipid particles) to a mammalian subject for the treatment of a disease or disorder such as a cell proliferative disorder (e.g., cancer).

In certain aspects, the present invention provides methods for introducing an siRNA that silences CSN5 gene expression into a cell, the method comprising contacting the cell with a nucleic acid-lipid particle described herein.

In certain other aspects, the present invention provides methods for the in vivo delivery of an siRNA that silences CSN5 gene expression, the method comprising administering to a mammalian subject a nucleic acid-lipid particle described herein.

In further aspects, the present invention provides methods for treating a cell proliferative disorder such as cancer in a mammalian subject in need thereof, the method comprising administering to the mammalian subject a therapeutically effective amount of a nucleic acid-lipid particle described herein. The particles of the invention are particularly effective at treating cancers of the liver, e.g., hepatocellular carcinoma (HCC) and liver metastatic disease.

The nucleic acid-lipid particles of the invention (e.g., SNALP) are advantageous and suitable for use in the administration of interfering RNA such as siRNA, aiRNA, and/or miRNA to a subject (e.g., a mammal such as a human) because they are stable in circulation, of a size required for pharmacodynamic behavior resulting in access to extravascular sites, and are capable of reaching target cell populations.

Other objects, features, and advantages of the present invention will be apparent to one of skill in the art from the following detailed description and figures.

BRIEF DESCRIPTION OF THE DRAWINGS

FIGS. 4A-4D illustrate data demonstrating that CSN5 gene silencing decreased HCC cell survival in a cell viability assay and reduced CSN5 mRNA levels in a quantitative real-time RT-PCR assay. In particular, CSN5-2 siRNA potently inhibited the growth of Huh7 and HepG2 cells and silenced target gene expression at the mRNA level. (A, B) Growth inhibition of Huh7 (A) or HepG2 (B) cells after transfection with 15 nM of three CSN5-specific siRNA was examined by an MTT assay 4 d after the treatment. The cells that were untreated (sham) and treated with NC siRNA were assayed simultaneously. Results are presented as mean percentage of absorbance at 540 nm±s.d. (C, D) Real-time RT-PCR analysis of CSN5 gene expression in Huh7 (C) or HepG2 (D) cells treated with the CSN5-specific siRNA. Total RNA was extracted at 48 h after treatment with 15 nM of the siRNA. In all PCR experiments, expression was calculated relative to GAPDH and is normalized to untreated control. Each bar value represents the mean±s.d. of triplicate experiments. NCsiRNA=negative control siRNA.

FIGS. 6A-6F illustrate data demonstrating that CSN5 gene silencing is associated with cell cycle arrest in the G1 phase. The effect of CSN5-2 siRNA on cell cycle progression of HCC cells was determined by cell cycle analysis after transfection of Huh7 or HepG2 cells with 15 nM of CSN5-2 siRNA for 48 h. The analysis was performed on an equal number of cells ($10^4$ events) by flow cytometry after staining of DNA with propium iodide. The cells that were untreated and treated with NCsiRNA were assayed simultaneously.

DETAILED DESCRIPTION OF THE INVENTION

I. Introduction

Figure 1A:
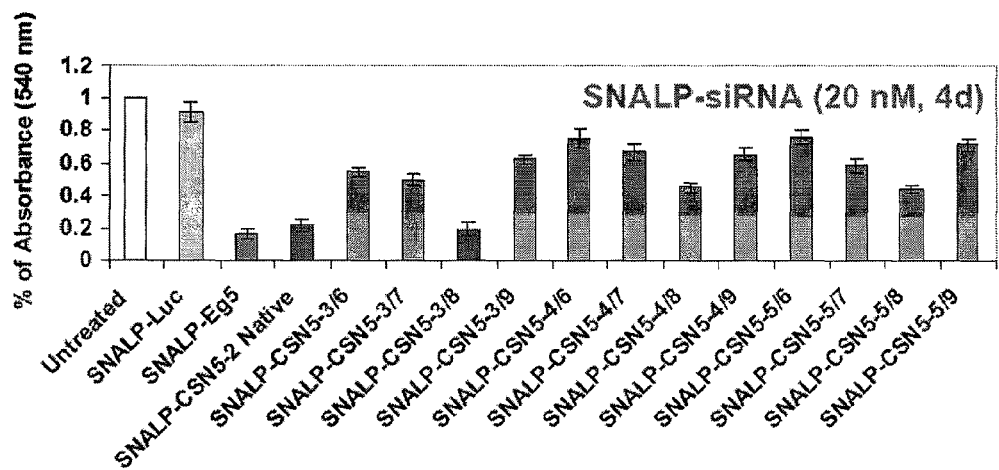
FIGS. 1A and 1B illustrate data demonstrating the effect of SNALP containing CSN5 siRNA on Huh7-1H6 cell growth. (A) Inhibition of Huh7-luc$^+$ cell growth after transfection with 20 nM of SNALP-formulated unmodified CSN5-2 siRNA or its modified variants. (B) Inhibition of Huh7-luc$^+$ cell growth after transfection with 15 nM of SNALP-formulated siRNA targeting other regions of the CSN5 gene. The siRNA transfectants were examined by an MTT assay 4 d after the treatment. As controls, the cells that were untreated and treated with luciferase-specific siRNA were assayed simultaneously. Results are shown as the mean percentage of absorbance at 540 nm±s.d.

Hepatocellular carcinoma (HCC) is a primary malignancy of the liver. Most cases of HCC are secondary to either a viral Hepatitis B or C infection or cirrhosis, with alcoholism being the most common cause of hepatic cirrhosis. HCC is the fifth most common cancer worldwide and the third most lethal neoplasm, accounting for about 600,000 deaths annually. Additional etiological factors believed to cause HCC include aflatoxin-B1, type II diabetes, and obesity. The usual outcome of HCC is poor because only 10-20% of hepatocellular carcinomas can be removed completely using surgery. If the cancer cannot be completely removed, the disease is usually deadly within 3 to 6 months. In fact, there is only an 8.9% 5-year survival rate of individuals with HCC in the United States. Recently, the multi-kinase inhibitor Sorafenib has been approved for the treatment of unresectable HCC based on phase III data showing improvements in survival time (10.7 mo versus 7.9 mo for placebo) of patients with advanced disease (Llovet et al., *J. Hepatol.*, 48 Suppl 1:S20-37 (2008)). With no other treatment options currently available, it is likely that Sorafenib will become part of the standard of care for this patient population.

The liver is also a common site of tumor metastatic disease. For example, approximately 50% of colorectal cancer patients develop metastases to the liver, resulting in significant increase in patient mortality (Steele et al., *Annals Surgery*, 210:127-138 (1989)). Combinatorial therapy with systemically administered conventional and targeted chemotherapeutics improves the survival times of these patients. However, the non-surgical cure for metastatic colon cancer remains elusive.

As such, it is clear that HCC and metastatic disease in the liver represent a significant unmet medical need that requires the development of novel therapeutic agents for more effective treatment options.

The present invention is based in part on the discovery that silencing CSN5 gene expression is an effective means to halt proliferation of rapidly dividing cells, e.g., cancer cells of the liver. In certain aspects, the present invention provides interfering RNA such as siRNA that target CSN5 gene expression, e.g., to decrease HCC cell survival and/or reduce HCC cell growth. In certain other aspects, the present invention provides nucleic acid-lipid particles (e.g., SNALP) comprising interfering RNA such as siRNA that silence CSN5 gene expression. It is a discovery of the present invention that the nucleic acid-lipid particles (e.g., SNALP) described herein are particularly effective for the treatment of liver cancers such as HCC and liver metastatic disease by encapsulating and delivering interfering RNA such as siRNA that target CSN5 gene expression in cancer cells of the liver. In particular, the in vivo administration of nucleic acid-lipid particles (e.g., SNALP) comprising CSN5 siRNA can effectively suppress neoplastic growth in a mouse model of HCC.

The present invention further provides methods of silencing CSN5 gene expression by administering nucleic acid-lipid particles (e.g., SNALP) comprising interfering RNA such as CSN5 siRNA to a mammalian subject. Moreover, the present invention provides methods of treating a subject who suffers from a cell proliferative disorder, e.g., liver cancer such as HCC or liver metastatic disease, by administering nucleic acid-lipid particles (e.g., SNALP) comprising interfering RNA such as CSN5 siRNA.

Therefore, targeted silencing of CSN5 by interfering RNA such as siRNA holds considerable promise as a novel therapeutic strategy for treating cancers such as liver cancers (e.g., HCC, liver metastatic disease, etc.). However, certain unmodified CSN5 siRNA sequences can be immunostimulatory, e.g., stimulate potent inflammatory responses from innate immune cells. The present invention overcomes this limitation by providing, in some aspects, CSN5 siRNA molecules with reduced or abrogated immunostimulatory properties. As a non-limiting example, the present invention provides CSN5 siRNA molecules that are less immunostimulatory than a corresponding unmodified CSN5 siRNA sequence using the selective incorporation of modified nucleotides such as 2'-O-methyl (2'OMe) uridine and/or guanosine nucleotides into either or both strands of the CSN5 siRNA sequence. In certain preferred embodiments, the immunostimulatory properties of CSN5 siRNA molecules and their ability to silence CSN5 expression can be balanced or optimized by the introduction of minimal and selective 2'OMe modifications within the double-stranded region of the siRNA duplex. Advantageously, this can be achieved at therapeutically viable CSN5 siRNA doses without cytokine induction, toxicity, and off-target effects associated with the use of certain unmodified CSN5 siRNA sequences.

As illustrated in the Examples herein, siRNA molecules targeting CSN5 gene expression were effective in inhibiting HCC cell growth in vitro. Specifically, Huh7 and HepG2 cells transfected with CSN5-2 siRNA for 4 days showed 68% and 77% growth inhibition, respectively, which was associated with cell-cycle arrest in the G1 phase. CSN5-deficient cells also exhibited a 1.8-fold increase in apoptosis as compared with negative control siRNA-treated cells, a property which was directly correlated with functional restoration of p53 and p27. In addition, silencing of CSN5 gene expression reduced the proportion of side population cells (50% and 70% in Huh7 and HepG2 cells, respectively), indicating that targeting the CSN5 gene is an effective form of anti-cancer stem cell therapy. Importantly, in vivo systemic delivery of 2'OMe-modified CSN5 siRNA encapsulated within stable nucleic acid-lipid-particles (SNALP) effectively suppressed neoplastic growth in an orthotopic mouse model of metastatic human liver cancer. Taken together, these results show that CSN5 is an important regulator of HCC cell growth and survival, and is an attractive target for the treatment of HCC. Furthermore, since CSN5-mediated degradation of p53 is a universal epigenetic event that promotes tumor development, the utility of targeting CSN5 gene expression is applicable to other cancers (in addition to liver cancers such as HCC) that overexpress CSN5 during the carcinogenic process.

Accordingly, the siRNA molecules of the present invention, when delivered using a safe and effective systemic delivery vehicle, are able to affect therapeutic CSN5 gene silencing through the confirmed mechanism of RNAi in the absence of unintended immune stimulation.

II. Definitions

As used herein, the following terms have the meanings ascribed to them unless specified otherwise.

The term "COP9 signalosome subunit 5," "CSN5," "Jun activating binding protein," or "Jab1" refers to the fifth subunit of the COP9 signalosome (CSN), a highly conserved protein complex that functions as an important regulator in multiple signaling pathways. The structure and function of the CSN complex is similar to that of the 19S regulatory particle of the 26S proteasome. The CSN complex has been shown to interact and act as a positive regulator of SCF-type E3 ubiquitin ligases (Deng et al., *Trends Genet.*, 16:289 (2000); Chamovitz et al., *EMBO Rep.*, 2:96-101 (2001)). In particular, the CSN complex targets p53 for its degradation through the ubiquitin system in coordination with human homolog of murine double minute 2 (Hdm2). CSN5 is a multifunctional protein that interacts with a variety of proteins either as a subunit of CSN complexes or alone, and is expressed in a wide array of eukaryotes from plants to human. CSN5 functions by interacting with a number of diverse proteins, including c-Jun, MIF1, integrin LFA-1, progesterone receptor, SRC-1, lutropin receptor, psoriasin, Smad4, and Bcl-3 (Emberley et al., *Cancer Res.*, 63:1954-1961 (2003); Tomoda et al., *Nature*, 398:160-165 (1999); Claret et al., *Nature*, 383:453-457 (1996); Wan et al., *EMBO Rep.*, 3:171-176 (2002); Bianchi et al., *Nature*, 404:617-621 (2000); Chauchereau et al., *J. Biol. Chem.*, 275:8540-8548 (2000); Li et al., *J. Biol. Chem.*, 275:13386-13393 (2000); Dechend et al., *Oncogene*, 18:3316-3323 (1999)). CSN5 also interacts and promotes the degradation of p27, a negative regulator of cell cycle progression (Tomoda et al., *J. Biol. Chem.*, 277: 2302-2310 (2002); Tomoda et al., *Nature*, 398:160-165

(1999)). CSN5 knock-out mice express high levels of p53 and p27, further implicating the importance of CSN5 in regulating the expression of tumor suppressor genes under normal conditions. Exemplary human CSN5 mRNA sequences are set forth in Genbank Accession Nos. NM_006837 (SEQ ID NO:34), BC001187, BC001859, BC007272, U65928, and U70734. An exemplary human CSN5 genomic sequence is set forth in Genbank Accession No. NC_000008 REGION: complement (68117868 . . . 68137116). An exemplary mouse CSN5 mRNA sequence is set forth in Genbank Accession No. NM_013715. CSN5 is also known as COPS5, SGN5, MOV-34, and MGC3149.

The term "interfering RNA" or "RNAi" or "interfering RNA sequence" refers to single-stranded RNA (e.g., mature miRNA) or double-stranded RNA (i.e., duplex RNA such as siRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA, aiRNA, miRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

An "effective amount" or "therapeutically effective amount" of an interfering RNA is an amount sufficient to produce the desired effect, e.g., an inhibition of expression of a target sequence in comparison to the normal expression level detected in the absence of an interfering RNA. Inhibition of expression of a target gene or target sequence is achieved when the value obtained with an interfering RNA relative to the control is about 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-10, IL-12, IL-13, TGF, and combinations thereof.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$, is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

A preferred example of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/).

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (P1, PAC, BAC, YAC, artificial chromosomes), expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, tRNA, viral RNA (vRNA), and combinations thereof.

Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

A "lipid particle" is used herein to refer to a lipid formulation that can be used to deliver a nucleic acid (e.g., an interfering RNA) to a target site of interest. In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the nucleic acid may be encapsulated in the lipid portion of the nucleic acid-lipid particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., siRNA, aiRNA, miRNA, ssDNA, dsDNA, ssRNA, short hairpin RNA (shRNA), dsRNA, or a plasmid, including plasmids from which an interfering RNA is transcribed) is fully encapsulated within the lipid. As used herein, the term "SNALP" includes an SPLP, which is the term used to refer to a nucleic acid-lipid particle comprising a nucleic acid (e.g., a plasmid) encapsulated within the lipid. SNALP and SPLP typically contain a cationic lipid, a non-cationic lipid, and optionally a lipid conjugate (e.g., a PEG-lipid conjugate). SNALP and SPLP are extremely useful for systemic applications, as they can exhibit extended circulation lifetimes following intravenous (i.v.) injection, they can accumulate at distal sites (e.g., sites physically separated from the administration site), and they can mediate expression of the transfected gene or silencing of target gene expression at these distal sites. SPLP include "pSPLP," which comprise an encapsulated condensing agent-nucleic acid complex as set forth in PCT Publication No. WO 00/03683, the disclosure of which is herein incorporated by reference in its entirety for all purposes.

The nucleic acid-lipid particles of the present invention (e.g., SNALP) typically have a mean diameter of from about 40 nm to about 150 nm, from about 50 nm to about 150 nm, from about 60 nm to about 130 nm, from about 70 nm to about 110 nm, or from about 70 to about 90 nm, and are substantially non-toxic. In addition, nucleic acids, when present in the nucleic acid-lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides an active agent or therapeutic agent, such as a nucleic acid (e.g., an interfering RNA), with full encapsulation, partial encapsulation, or both. In a preferred embodiment, the nucleic acid is fully encapsulated in the lipid particle (e.g., to form an SPLP, pSPLP, SNALP, or other nucleic acid-lipid particle).

The term "lipid conjugate" refers to a conjugated lipid that inhibits aggregation of lipid particles. Such lipid conjugates include, but are not limited to, polyamide oligomers (e.g., ATTA-lipid conjugates), PEG-lipid conjugates, such as PEG coupled to dialkyloxypropyls, PEG coupled to diacylglycerols, PEG coupled to cholesterol, PEG coupled to phosphatidylethanolamines, PEG conjugated to ceramides (see, e.g., U.S. Pat. No. 5,885,613, the disclosure of which is herein incorporated by reference in its entirety for all purposes), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In preferred embodiments, non-ester containing linker moieties are used.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH (e.g., pH of about 7.0). It has been surprisingly found that cationic lipids comprising alkyl chains with multiple sites of unsaturation, e.g., at least two or three sites of unsaturation, are particularly useful for forming lipid particles with increased membrane fluidity. A number of cationic lipids and related analogs, which are also useful in the present invention, have been described in U.S. Patent Publication Nos. 20060083780 and 20060240554; U.S. Pat. Nos. 5,208,036; 5,264,618; 5,279,833; 5,283,185; 5,753,613; and 5,785,992; and PCT Publication No. WO 96/10390, the disclosures of which are herein incorporated by reference in their entirety for all purposes. Non-limiting examples of cationic lipids are described in detail herein. In some cases, the cationic lipids comprise a protonatable tertiary amine (e.g., pH titratable) head group, C18 alkyl chains, ether linkages between the head group and alkyl chains, and 0 to 3 double bonds. Such lipids include, e.g., DSDMA, DLinDMA, DLenDMA, and DODMA.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent or therapeutic agent such as an interfering RNA within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent or therapeutic agent such as an interfering RNA directly to a target site within an organism. For example, an agent can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma. As used herein, a "tumor" comprises one or more cancerous cells.

III. Description of the Embodiments

The present invention provides compositions comprising nucleic acids (e.g., interfering RNA such as siRNA, aiRNA, miRNA, etc.) that target CSN5 expression and methods of using such compositions to silence CSN5 expression.

In one aspect, the present invention provides an siRNA molecule comprising a double-stranded region of about 15 to about 60 nucleotides in length, wherein the siRNA molecule is capable of silencing CSN5 gene expression.

In certain embodiments, the siRNA molecule comprises a double-stranded region of about 15-50, 15-40, 15-35, 15-30, 15-25, or 19-25 nucleotides in length, or 15, 16, 17, 18, 19, 20, 21, 22, 23, 24, or 25 nucleotides in length. The siRNA molecules of the present invention are capable of silencing CSN5 gene expression in vitro and/or in vivo.

In some embodiments, the siRNA molecule comprises at least one modified nucleotide. In certain preferred embodiments, the siRNA molecule comprises one, two, three, four, five, six, seven, eight, nine, ten, or more modified nucleotides in the double-stranded region. In certain instances, the siRNA comprises from about 1% to about 100% (e.g., about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region. In preferred embodiments, less than about 25% (e.g., less than about 25%, 20%, 15%, 10%, or 5%) or from about 1% to about 25% (e.g., from about 1%-25%, 5%-25%, 10%-25%, 15%-25%, 20%-25%, or 10%-20%) of the nucleotides in the double-stranded region comprise modified nucleotides.

In other embodiments, the siRNA molecule comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof. In certain instances, the siRNA does not comprise 2'OMe-cytosine nucleotides. In other embodiments, the siRNA comprises a hairpin loop structure.

The siRNA may comprise modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some preferred embodiments, a modified siRNA molecule is less immunostimulatory than a corresponding unmodified siRNA sequence. In such embodiments, the modified siRNA molecule with reduced immunostimulatory properties advantageously retains RNAi activity against the target CSN5 sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In certain embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 80%, 85%, 90%, 95%, or 100% of the expression of the target CSN5 sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. Preferably, the siRNA has 3' overhangs of two nucleotides on each side of the double-stranded region. In certain instances, the 3' overhang on the antisense strand has complementarity to the target sequence and the 3' overhang on the sense strand has complementarity to a complementary strand of the target sequence. Alternatively, the 3' overhangs do not have complementarity to the target sequence or the complementary strand thereof. In some embodiments, the 3' overhangs comprise one, two, three, four, or more nucleotides such as 2'-deoxy (2'H) nucleotides. In certain preferred embodiments, the 3' overhangs comprise deoxythymidine (dT) and/or uridine nucleotides. In other embodiments, one or more of the nucleotides in the 3' overhangs on one or both sides of the double-stranded region comprise modified nucleotides. Non-limiting examples of modified nucleotides are described above and include 2'OMe nucleotides, 2'-deoxy-2'F nucleotides, 2'-deoxy nucleotides, 2'-O-2-MOE nucleotides, LNA nucleotides, and mixtures thereof. In preferred embodiments, one, two, three, four, or more nucleotides in the 3' overhangs present on the sense and/or antisense strand of the siRNA comprise 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof.

The siRNA may comprise at least one or a cocktail (e.g., at least two, three, four, five, six, seven, eight, nine, ten, or more) of unmodified and/or modified siRNA sequences that silence CSN5 gene expression. The cocktail of siRNA may comprise sequences which are directed to the same region or domain (e.g., a "hot spot") and/or to different regions or domains of the CSN5 gene. In certain instances, one or more (e.g., at least two, three, four, five, six, seven, eight, nine, ten, or more) modified siRNA that silence CSN5 gene expression are present in a cocktail. In certain other instances, one or more (e.g., at least two, three, four, five, six, seven, eight, nine, ten, or more) unmodified siRNA sequences that silence CSN5 gene expression are present in a cocktail.

In some embodiments, the antisense strand of the siRNA molecule comprises or consists of a sequence that is at least about 80%, 85%, 90%, 95%, 96%, 97%, 98%, or 99% complementary to a target CSN5 sequence or a portion thereof, e.g., one of the target CSN5 sequences set forth in Table 1. In other embodiments, the antisense strand of the siRNA molecule comprises or consists of a sequence that is 100% complementary to a target CSN5 sequence or a portion thereof, e.g., one of the target CSN5 sequences set forth in Table 1. In further embodiments, the antisense strand of the siRNA molecule comprises or consists of a sequence that specifically hybridizes to a target CSN5 sequence or a portion thereof, e.g., one of the target CSN5 sequences set forth in Table 1. As a non-limiting example, the antisense strand of the CSN5 siRNA molecule may comprise or consist of one of the antisense strand sequences set forth in Tables 1-2.

In certain embodiments, the sense strand of the siRNA molecule comprises or consists of a sequence that is at least about 80%, 85%, 90%, 95%, 96%, 97%, 98%, or 99% identical to a target CSN5 sequence or a portion thereof, e.g., one of the target CSN5 sequences set forth in Table 1. In certain other embodiments, the sense strand of the siRNA molecule comprises or consists of a sequence that is 100% identical to a target CSN5 sequence or a portion thereof, e.g., one of the target CSN5 sequences set forth in Table 1. As a non-limiting example, the sense strand of the CSN5 siRNA molecule may comprise or consist of one of the sense strand sequences set forth in Tables 1-2.

In preferred embodiments, the siRNA comprises one or more (e.g., at least two, three, four, five, six, seven, eight, nine, ten, or more) of the sequences (e.g., sense and/or antisense strand sequences) set forth in Tables 1-2. The CSN5 siRNA sense and/or antisense strand sequence can be an unmodified (i.e., native) sequence set forth in Table 1 or can be a chemically modified version thereof (e.g., comprising 2'OMe-nucleotides). In particularly preferred embodiments, the siRNA comprises or consists of the CSN5-2 sense strand (SEQ ID NO:3) and antisense strand (SEQ ID NO:4) sequences set forth in Table 1 or chemically modified versions thereof. Non-limiting examples of modified CSN5-2 siRNA are set forth in Table 2. Preferably, the modified CSN5-2 siRNA comprises or consists of the CSN5-3/8 sense strand (SEQ ID NO:27) and antisense strand (SEQ ID NO:30) sequences set forth in Table 2.

In other embodiments, the present invention provides a pharmaceutical composition comprising an siRNA molecule described herein and a pharmaceutically acceptable carrier.

In another aspect, a nucleic acid of the present invention (e.g., an interfering RNA such as siRNA, aiRNA, miRNA, etc.) further comprises a carrier system. In certain instances, the carrier system is selected from the group consisting of a nucleic acid-lipid particle (e.g., SNALP), a liposome, a micelle, a virosome, a nucleic acid complex, and mixtures thereof. Generally, the nucleic acid complex may comprise the nucleic acid (e.g., interfering RNA) complexed with a cationic lipid, a cationic polymer, a cyclodextrin, or mixtures thereof. As a non-limiting example, an siRNA molecule may be complexed with a cationic polymer, wherein the cationic polymer is polyethylenimine (PEI). In preferred embodiments, the carrier system is a nucleic acid-lipid particle such as a SNALP and the nucleic acid is an siRNA. In other embodiments, the carrier system is a nucleic acid-lipid particle such as a SNALP and the nucleic acid is an aiRNA, miRNA, or a single-stranded or double-stranded DNA, RNA, or a DNA/RNA hybrid including, but not limited to, an antisense oligonucleotide, a ribozyme, a plasmid, an immunostimulatory oligonucleotide, or mixtures thereof.

In some embodiments, the present invention provides a nucleic acid-lipid particle (e.g., SNALP) that targets CSN5 gene expression. The nucleic acid-lipid particle typically comprises an interfering RNA such as an siRNA that silences CSN5 gene expression, a cationic lipid, and a non-cationic lipid. In certain instances, the nucleic acid-lipid particle may further comprise a conjugated lipid that inhibits aggregation of particles. In preferred embodiments, the nucleic acid-lipid particle comprises an siRNA that silences CSN5 gene expression, a cationic lipid, a non-cationic lipid, and a conjugated lipid that inhibits aggregation of particles.

In the nucleic acid-lipid particles of the invention (e.g., SNALP comprising an interfering RNA such as siRNA), the cationic lipid may comprise, e.g., one or more of the following: 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5]-(cholest-5-en-3-beta-oxy)-3'-oxapentoxy)-3-dimethyl-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. In certain preferred embodiments, the cationic lipid is DLinDMA, DLin-K-C2-DMA ("XTC2"), or mixtures thereof.

The synthesis of cationic lipids such as DLin-K-C2-DMA ("XTC2"), DLin-K-C3-DMA, DLin-K-C4-DMA, DLin-K6-DMA, and DLin-K-MPZ, as well as additional cationic lipids, is described in U.S. Provisional Application No. 61/104,212, filed Oct. 9, 2008, the disclosure of which is herein incorporated by reference in its entirety for all purposes. The synthesis of cationic lipids such as DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DOAP, and DLin-EG-DMA, as well as additional cationic lipids, is described in PCT Application No. PCT/US08/88676, filed Dec. 31, 2008, the disclosure of which is herein incorporated by reference in its entirety for all purposes. The synthesis of cationic lipids such as CLinDMA, as well as additional cationic lipids, is described in U.S. Patent Publication No. 20060240554, the disclosure of which is herein incorporated by reference in its entirety for all purposes.

In some embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle. In certain instances, the cationic lipid may comprise from about 55 mol % to about 80 mol %, from about 55 mol % to about 75 mol %, from about 55 mol % to about 70 mol %, from about 55 mol % to about 65 mol %, from about 60 mol % to about 80 mol %, from about 60 mol % to about 75 mol %, or from about 60 mol % to about 70 mol % of the total lipid present in the particle. In certain other instances, the cationic lipid may comprise (at least) about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

In other embodiments, the cationic lipid may comprise from about 2 mol % to about 60 mol %, from about 2 mol % to about 50 mol %, from about 5 mol % to about 45 mol %, from about 5 mol % to about 30 mol %, from about 5 mol % to about 15 mol %, from about 10 mol % to about 50 mol %, from about 20 mol % to about 50 mol %, from about 30 mol % to about 50 mol %, from about 40 mol % to about 50 mol %, or about 40 mol % of the total lipid present in the particle. In certain instances, the cationic lipid may comprise (at least) about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mol % (or any fraction thereof or range therein) of the total lipid present in the particle.

In the nucleic acid-lipid particles of the invention (e.g., SNALP comprising an interfering RNA such as siRNA), the non-cationic lipid may comprise, e.g., one or more anionic lipids and/or neutral lipids. In preferred embodiments, the non-cationic lipid comprises one of the following neutral lipid components: (1) cholesterol or a derivative thereof; (2) a phospholipid; or (3) a mixture of a phospholipid and cholesterol or a derivative thereof.

Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The synthesis of cholesteryl-2'-hydroxyethyl ether is described in U.S. Provisional Application No. 61/045,228, filed Apr. 15, 2008, the disclosure of which is herein incorporated by reference in its entirety for all purposes.

The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain preferred embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

In certain instances, the non-cationic lipid (e.g., one or more phospholipids and/or cholesterol) may comprise from about 10 mol % to about 49.5 mol %, from about 13 mol % to about 49.5 mol %, from about 15 mol % to about 49.5 mol %, from about 20 mol % to about 49.5 mol %, from about 25 mol % to about 49.5 mol %, from about 30 mol % to about 49.5 mol %, from about 35 mol % to about 49.5 mol %, or from about 40 mol % to about 49.5 mol % of the total lipid present in the particle.

In certain other instances, the non-cationic lipid (e.g., one or more phospholipids and/or cholesterol) may comprise (at least) about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol % (or any fraction thereof or range therein) of the total lipid present in the particle.

In certain preferred embodiments, the non-cationic lipid comprises cholesterol or a derivative thereof of from about 31.5 mol % to about 42.5 mol % of the total lipid present in the particle. As a non-limiting example, a phospholipid-free nucleic acid-lipid particle of the invention may comprise cholesterol or a derivative thereof at about 37 mol % of the total lipid present in the particle. In other preferred embodiments, a phospholipid-free nucleic acid-lipid particle of the invention may comprise cholesterol or a derivative thereof of from about 30 mol % to about 45 mol %, from about 30 mol % to about 40 mol %, from about 30 mol % to about 35 mol %, from about 35 mol % to about 45 mol %, from about 40 mol % to about 45 mol %, from about 32 mol % to about 45 mol %, from about 32 mol % to about 42 mol %, from about 32 mol % to about 40 mol %, from about 34 mol % to about 45 mol %, from about 34 mol % to about 42 mol %, from about 34 mol % to about 40 mol %, or about 30, 31, 32, 33, 34, 35; 36, 37, 38, 39, 40, 41, 42, 43, 44, or 45 mol % (or any fraction thereof or range therein) of the total lipid present in the particle.

In certain other preferred embodiments, the non-cationic lipid comprises a mixture of: (i) a phospholipid of from about 4 mol % to about 10 mol % of the total lipid present in the particle; and (ii) cholesterol or a derivative thereof of from about 30 mol % to about 40 mol % of the total lipid present in the particle. As a non-limiting example, a nucleic acid-lipid particle comprising a mixture of a phospholipid and cholesterol may comprise DPPC at about 7 mol % and cholesterol at about 34 mol % of the total lipid present in the particle. In other embodiments, the non-cationic lipid comprises a mixture of: (i) a phospholipid of from about 3 mol % to about 15 mol %, from about 4 mol % to about 15 mol %, from about 4 mol % to about 12 mol %, from about 4 mol % to about 10 mol %, from about 4 mol % to about 8 mol %, from about 5 mol % to about 12 mol %, from about 5 mol % to about 9 mol %, from about 6 mol % to about 12 mol %, from about 6 mol % to about 10 mol %, or about 3, 4, 5, 6, 7, 8, 9, 10, 11, 12, 13, 14, or 15 mol % (or any fraction thereof or range therein) of the total lipid present in the particle; and (ii) cholesterol or a derivative thereof of from about 25 mol % to about 45 mol %, from about 30 mol % to about 45 mol %, from about 25 mol % to about 40 mol %, from about 30 mol % to about 40 mol %, from about 25 mol % to about 35 mol %, from about 30 mol % to about 35 mol %, from about 35 mol % to about 45 mol %, from about 40 mol % to about 45 mol %, from about 28 mol % to about 40 mol %, from about 28 mol % to about 38 mol %, from about 30 mol % to about 38 mol %, from about 32 mol % to about 36 mol %, or about 25, 26, 27, 28, 29, 30, 31, 32, 33, 34, 35, 36, 37, 38, 39, 40, 41, 42, 43, 44, or 45 mol % (or any fraction thereof or range therein) of the total lipid present in the particle.

In other embodiments, the non-cationic lipid may comprise from about 5 mol % to about 90 mol %, from about 10 mol % to about 85 mol %, from about 20 mol % to about 85 mol %, from about 5 mol % to about 80 mol %, from about 10 mol % to about 80 mol %, from about 20 mol % to about 80 mol %, about 10 mol % (e.g., phospholipid such as DSPC or DPPC only), or about 60 mol (e.g., about 10 mol % of a phospholipid such as DSPC or DPPC and about 48 mol % cholesterol) of the total lipid present in the particle. In these embodiments, the cholesterol or cholesterol derivative may be from 0 mol % to about 10 mol %, from about 2 mol % to about 10 mol %, from about 10 mol % to about 60 mol %, from about 20 mol % to about 45 mol %, from about 30 mol % to about 50 mol %, from about 40 mol % to about 60 mol %, or about 48 mol % of the total lipid present in the particle.

In the nucleic acid-lipid particles of the invention (e.g., SNALP comprising an interfering RNA such as siRNA), the conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676, filed Dec. 31, 2008, the disclosure of which is herein incorporated by reference in its entirety for all purposes. Yet additional PEG-lipid conjugates suitable for use in the invention include, without limitation, 1-[8'-(1,2-dimyristoyl-3-propanoxy)-carboxamido-3',6'-dioxaoctanyl] carbamoyl-ω-methyl-poly(ethylene glycol) (2 KPEG-DMG). The synthesis of 2 KPEG-DMG is described in U.S. Pat. No. 7,404,969, the disclosure of which is herein incorporated by reference in its entirety for all purposes.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In some embodiments, the conjugated lipid that inhibits aggregation of particles is a CPL that has the formula: A-W-Y, wherein A is a lipid moiety, W is a hydrophilic polymer, and Y is a polycationic moiety. W may be a polymer selected from the group consisting of polyethyleneglycol (PEG), polyamide, polylactic acid, polyglycolic acid, polylactic acid/polyglycolic acid copolymers, or combinations thereof, the polymer having a molecular weight of from about 250 to about 7000 daltons. In some embodiments, Y has at least 4 positive charges at a selected pH. In some embodiments, Y may be lysine, arginine, asparagine, glutamine, derivatives thereof, or combinations thereof.

In certain instances, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle.

In certain other instances, the conjugated lipid that prevents aggregation of particles may comprise from 0 mol % to about 20 mol %, from about 0.5 mol % to about 20 mol %, from about 1 mol % to about 15 mol %, from about 1 mol % to about 10 mol %, from about 2 mol % to about 10 mol %, from about 4 mol % to about 10 mol %, from about 5 mol % to about 10 mol %, about 0.5 mol %, about 1 mol %, about 1.5 mol %, about 2 mol %, about 2.5 mol %, about 3 mol %, about 3.5 mol %, about 4 mol %, about 4.5 mol %, about 5 mol %, about 5.5 mol %, about 6 mol %, about 6.5 mol %, about 7 mol %, about 7.5 mol %, about 8 mol %, about 8.5 mol %, about 9 mol %, about 9.5 mol %, or about 10 mol % of the total lipid present in the particle.

In the nucleic acid-lipid particles of the invention (e.g., SNALP comprising an interfering RNA such as siRNA), the nucleic acid may be fully encapsulated within the lipid portion of the particle, thereby protecting the nucleic acid from nuclease degradation. In preferred embodiments, a SNALP comprising a nucleic acid such as an interfering RNA (e.g., siRNA) is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. In the context of nucleic acids, full encapsulation may be determined by an Oligreen® assay. Oligreen® is an ultra-sensitive fluorescent nucleic acid stain for quantitating oligonucleotides and single-stranded DNA or RNA in solution (available from Invitrogen Corporation; Carlsbad, Calif.). "Fully encapsulated" also indicates that the nucleic acid-lipid particles are serum-stable, that is, that they do not rapidly decompose into their component parts upon in vivo administration.

In another aspect, the present invention provides a nucleic acid-lipid particle (e.g., SNALP) composition comprising a plurality of nucleic acid-lipid particles. In preferred embodiments, the nucleic acid is fully encapsulated within the lipid portion of the nucleic acid-lipid particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, %, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the nucleic acid-lipid particles have the nucleic acid encapsulated therein.

Typically, the nucleic acid-lipid particles (e.g., SNALP) of the invention have a lipid:nucleic acid ratio (mass/mass ratio) of from about 1 to about 100. In some instances, the lipid:nucleic acid ratio (mass/mass ratio) ranges from about 1 to about 50, from about 2 to about 25, from about 3 to about 20, from about 4 to about 15, or from about 5 to about 10. In preferred embodiments, the nucleic acid-lipid particles have a lipid:nucleic acid ratio (mass/mass ratio) of from about 5 to about 15, e.g., about 5, 6, 7, 8, 9, 10, 11, 12, 13, 14, or 15 (or any fraction thereof or range therein).

Typically, the nucleic acid-lipid particles (e.g., SNALP) of the invention have a mean diameter of from about 40 nm to about 150 nm. In preferred embodiments, the nucleic acid-lipid particles of the invention have a mean diameter of from about 40 nm to about 130 nm, from about 40 nm to about 120 nm, from about 40 nm to about 100 nm, from about 50 nm to about 120 nm, from about 50 nm to about 100 nm, from about 60 nm to about 120 nm, from about 60 nm to about 110 nm, from about 60 nm to about 100 nm, from about 60 nm to about 90 nm, from about 60 nm to about 80 nm, from about 70 nm to about 120 nm, from about 70 nm to about 110 nm, from about 70 nm to about 100 nm, from about 70 nm to about 90 nm, from about 70 nm to about 80 nm, or less than about 120 nm, 110 nm, 100 nm, 90 nm, or 80 nm (or any fraction thereof or range therein).

In certain embodiments, the present invention provides nucleic acid-lipid particles (e.g., SNALP) comprising: (a) one or more nucleic acids (e.g., interfering RNA such as siRNA, aiRNA, miRNA) that silence CSN5 gene expression; (b) one or more cationic lipids comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle. The nucleic acid-lipid particles within these embodiments are further described in U.S. Provisional Application No. 61/045,228, filed Apr. 15, 2008, the disclosure of which is herein incorporated by reference in its entirety for all purposes.

In one specific embodiment of the invention, the nucleic acid-lipid particle (e.g., SNALP) comprises: (a) one or more unmodified and/or modified interfering RNA (e.g., siRNA, aiRNA, miRNA) that silence CSN5 gene expression; (b) a cationic lipid comprising from about 56.5 mol % to about 66.5 mol % of the total lipid present in the particle; (c) a non-cationic lipid comprising from about 31.5 mol % to about 42.5 mol % of the total lipid present in the particle; and (d) a conjugated lipid that inhibits aggregation of particles comprising from about 1 mol % to about 2 mol % of the total lipid present in the particle. This specific embodiment is generally referred to herein as the "1:62" formulation. In a preferred embodiment, the cationic lipid is DLinDMA or DLin-K-C2-DMA ("XTC2"), the non-cationic lipid is cholesterol, and the conjugated lipid is a PEG-DAA conjugate. Although these are preferred embodiments of the 1:62 formulation, those of skill in the art will appreciate that other cationic lipids, non-cationic lipids (including other cholesterol derivatives), and conjugated lipids can be used in the 1:62 formulation as described herein.

In another specific embodiment of the invention, the nucleic acid-lipid particle (e.g., SNALP) comprises: (a) one or more unmodified and/or modified interfering RNA (e.g., siRNA, aiRNA, miRNA) that silence CSN5 gene expression;

(b) a cationic lipid comprising from about 52 mol % to about 62 mol % of the total lipid present in the particle; (c) a non-cationic lipid comprising from about 36 mol % to about 47 mol % of the total lipid present in the particle; and (d) a conjugated lipid that inhibits aggregation of particles comprising from about 1 mol % to about 2 mol % of the total lipid present in the particle. This specific embodiment is generally referred to herein as the "1:57" formulation. In one preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 5 mol % to about 9 mol % of the total lipid present in the particle (e.g., about 7.1 mol %) and the cholesterol (or cholesterol derivative) comprises from about 32 mol % to about 37 mol % of the total lipid present in the particle (e.g., about 34.3 mol %), and the PEG-lipid is a PEG-DAA (e.g., PEG-cDMA). Although these are preferred embodiments of the 1:57 formulation, those of skill in the art will appreciate that other cationic lipids, non-cationic lipids (including other phospholipids and other cholesterol derivatives), and conjugated lipids can be used in the 1:57 formulation as described herein.

In yet another specific embodiment of the invention, the nucleic acid-lipid particle (e.g., SNALP) comprises: (a) one or more unmodified and/or modified interfering RNA (e.g., siRNA, aiRNA, miRNA) that silence CSN5 gene expression; (b) a cationic lipid comprising from about 30 mol % to about 50 mol % of the total lipid present in the particle; (c) a non-cationic lipid comprising from about 47 mol % to about 69 mol % of the total lipid present in the particle; and (d) a conjugated lipid that inhibits aggregation of particles comprising from about 1 mol % to about 3 mol % of the total lipid present in the particle. This specific embodiment is generally referred to herein as the "2:40" formulation. In one preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 5 mol % to about 15 mol % of the total lipid present in the particle (e.g., about 10 mol %) and the cholesterol (or cholesterol derivative) comprises from about 40 mol % to about 60 mol % of the total lipid present in the particle (e.g., about 48 mol %), and the PEG-lipid is a PEG-DAA (e.g., PEG-cDMA). Although these are preferred embodiments of the 2:40 formulation, those of skill in the art will appreciate that other cationic lipids, non-cationic lipids (including other phospholipids and other cholesterol derivatives), and conjugated lipids can be used in the 2:40 formulation as described herein.

In preferred embodiments, the 1:62 formulation is a three-component system which is phospholipid-free and comprises about 1.5 mol % PEG-cDMA (or PEG-cDSA), about 61.5 mol % DLinDMA (or XTC2), and about 36.9 mol % cholesterol (or derivative thereof). In other preferred embodiments, the 1:57 formulation is a four-component system which comprises about 1.4 mol % PEG-cDMA (or PEG-cDSA), about 57.1 mol % DLinDMA (or XTC2), about 7.1 mol % DPPC (or DSPC), and about 34.3 mol % cholesterol (or derivative thereof). In additional preferred embodiments, the 2:40 formulation is a four-component system which comprises about 2 mol % PEG-cDMA (or PEG-cDSA), about 40 mol % DLinDMA (or XTC2), about 10 mol % DPPC (or DSPC), and about 48 mol % cholesterol (or derivative thereof). It should be understood that these SNALP formulations are target formulations, and that the amount of lipid (both cationic and non-cationic) present and the amount of lipid conjugate present in the formulations may vary.

In some embodiments, the nucleic acid-lipid particles (e.g., SNALP) comprise 1, 2, 3, 4, 5, 6, 7, 8, 9, 10, or more unmodified and/or modified siRNA molecules comprising or consisting of the sequences set forth in Tables 1-2.

The present invention also provides a pharmaceutical composition comprising a nucleic acid-lipid particle (e.g., SNALP) described herein and a pharmaceutically acceptable carrier.

In a further aspect, the siRNA molecules described herein are used in methods for silencing CSN5 gene expression. In one embodiment, the present invention provides a method for introducing an siRNA that silences expression (e.g., mRNA and/or protein levels) of a CSN5 gene into a cell by contacting the cell with an siRNA molecule described herein. In another embodiment, the present invention provides a method for in vivo delivery of an siRNA molecule that silences expression of a CSN5 gene by administering to a mammal an siRNA molecule described herein. Administration of the siRNA molecule can be by any route known in the art, such as, e.g., oral, intranasal, intravenous, intraperitoneal, intramuscular, intra-articular, intralesional, intratracheal, subcutaneous, or intradermal.

In these methods, the siRNA molecule that silences CSN5 gene expression is typically formulated with a carrier system, and the carrier system comprising the siRNA is administered to a mammal requiring such treatment. Alternatively, cells are removed from a mammal such as a human, the siRNA is delivered in vitro using a carrier system, and the cells are then administered to the mammal, such as by injection. Examples of carrier systems suitable for use in the present invention include, but are not limited to, nucleic acid-lipid particles, liposomes, micelles, virosomes, nucleic acid complexes (e.g., lipoplexes, polyplexes, etc.), and mixtures thereof. The carrier system may comprise at least one or a cocktail (e.g., at least 2, 3, 4, 5, 6, 7, 8, 9, 10, or more) of siRNA molecules that silence CSN5 gene expression. In certain embodiments, the carrier system comprises at least one or a cocktail of the sequences set forth in Tables 1-2.

In some embodiments, the siRNA molecule that silences CSN5 gene expression is in a nucleic acid-lipid particle (e.g., SNALP) comprising the siRNA, a cationic lipid, and a non-cationic lipid. Preferably, the siRNA is in a nucleic acid-lipid particle comprising the siRNA, a cationic lipid, a non-cationic lipid, and a conjugated lipid that inhibits aggregation of particles. A therapeutically effective amount of the nucleic acid-lipid particle can be administered to a mammal (e.g., a rodent such as a mouse or a primate such as a human, chimpanzee, or monkey).

In preferred embodiments, the present invention provides a method for introducing one or more interfering RNA (e.g., siRNA, aiRNA, miRNA) that silence CSN5 gene expression into a cell, comprising contacting the cell with a nucleic acid-lipid particle (e.g., SNALP) described herein. In one embodiment, the cell is in a mammal and the mammal is a human. In another embodiment, the present invention provides a method for the in vivo delivery of one or more interfering RNA (e.g., siRNA, aiRNA, miRNA) that silence CSN5 gene expression, comprising administering to a mammalian subject a nucleic acid-lipid particle (e.g., SNALP) described herein. In a preferred embodiment, the mode of particle administration includes, but is not limited to, oral, intranasal, intravenous, intraperitoneal, intramuscular, intra-articular, intralesional, intratracheal, subcutaneous, and intradermal. Preferably, the mammalian subject is a human. In other embodiments, the delivery of the particles is to the liver, e.g., to liver tumor cells. In certain instances, the particles of the invention can be used to preferentially target the liver, e.g., to reach tumor cell populations in the liver.

In one embodiment, at least about 5%, 10%, 15%, 20%, or 25% of the total injected dose of the nucleic acid-lipid particles (e.g., SNALP) is present in plasma about 8, 12, 24, 36, or 48 hours after injection. In other embodiments, more than about 20%, 30%, 40% and as much as about 60%, 70% or 80% of the total injected dose of the particles is present in plasma about 8, 12, 24, 36, or 48 hours after injection. In certain instances, more than about 10% of a plurality of the particles is present in the plasma of a mammal about 1 hour after administration. In certain other instances, the presence of the particles is detectable at least about 1 hour after administration of the particle. In certain embodiments, the presence of an interfering RNA (e.g., siRNA) is detectable in tumor cells at about 8, 12, 24, 36, 48, 60, 72 or 96 hours after administration. In other embodiments, downregulation of expression of a target CSN5 sequence by an interfering RNA (e.g., siRNA) is detectable at about 8, 12, 24, 36, 48, 60, 72 or 96 hours after administration. In yet other embodiments, downregulation of expression of a target CSN5 sequence by an interfering RNA (e.g., siRNA) occurs preferentially in tumor cells. In further embodiments, the presence or effect of an interfering RNA (e.g., siRNA) in cells at a site proximal or distal to the site of administration or in tumor cells is detectable at about 12, 24, 48, 72, or 96 hours, or at about 6, 8, 10, 12, 14, 16, 18, 19, 20, 22, 24, 26, or 28 days after administration. In additional embodiments, the particles of the invention are administered parenterally or intraperitoneally.

In some embodiments, downregulation of the CSN5 gene is determined by detecting mRNA or protein levels in a biological sample from the mammal. In other embodiments, downregulation of expression of the CSN5 sequence is detected by measuring cell viability or the induction of apoptosis of cells in a biological sample from the mammal.

In some embodiments, the nucleic acid-lipid particles (e.g., SNALP) of the invention are particularly useful in methods for the therapeutic delivery of one or more nucleic acids comprising an interfering RNA sequence (e.g., siRNA). In particular, it is an object of this invention to provide in vitro and in vivo methods for treatment of a disease or disorder such as a cell proliferative disorder (e.g., cancer) in a mammal (e.g., a rodent such as a mouse or a primate such as a human, chimpanzee, or monkey) by downregulating or silencing the transcription and/or translation of the CSN5 gene. As a non-limiting example, the methods of the invention are useful for in vivo delivery of interfering RNA (e.g., siRNA) targeting the CSN5 gene to the tumor (e.g., liver tumor) of a mammalian subject.

Non-limiting examples of cell proliferative disorders include neoplasia (e.g., cancer), hyperplasia, restenosis, cardiac hypertrophy, immune disorders, and inflammation. Preferably, the cell proliferative disorder is a neoplastic disorder such as cancer. In some embodiments, the cancer includes, but is not limited to, liver cancer (e.g., hepatocellular carcinoma, secondary liver cancer, and hepatoblastoma), papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, leukemia, lymphoma, Hodgkin's disease, osteosarcoma, testicular cancer, and Burkitt's disease. The nucleic acid-lipid particles of the present invention are particularly effective at treating cancers of the liver, e.g., hepatocellular carcinoma.

In certain embodiments, the disease or disorder (e.g., cancer such as liver cancer) is associated with expression and/or overexpression of the CSN5 gene, and expression or overexpression of the gene is reduced by the interfering RNA (e.g., siRNA). In certain other embodiments, a therapeutically effective amount of the nucleic acid-lipid particle may be administered to the mammal, e.g., for the treatment of cancer such as liver cancer (e.g., hepatocellular carcinoma). In some instances, an interfering RNA (e.g., siRNA) is formulated into a SNALP, and the particles are administered to patients requiring such treatment. In other instances, cells are removed from a patient, the interfering RNA (e.g., siRNA) is delivered in vitro (e.g., using a SNALP described herein), and the cells are reinjected into the patient.

As such, the nucleic acid-lipid particles of the invention are advantageous and suitable for use in the administration of nucleic acids such as interfering RNA (e.g., siRNA) to a subject (e.g., a mammal such as a human) because they are stable in circulation, of a size required for pharmacodynamic behavior resulting in access to extravascular sites, and are capable of reaching target cell populations.

In another aspect, the present invention provides a method for modifying an immunostimulatory siRNA that silences CSN5 gene expression, the method comprising:
 (a) providing an unmodified siRNA sequence capable of silencing CSN5 gene expression, wherein the unmodified siRNA sequence has immunostimulatory properties and comprises a double-stranded sequence of about 15 to about 60 nucleotides in length; and
 (b) modifying the unmodified siRNA sequence by substituting one or more nucleotides with modified nucleotides,
 thereby generating a modified siRNA molecule that is less immunostimulatory thin the unmodified siRNA sequence and is capable of silencing CSN5 gene expression.

In some embodiments, the method further comprises: (c) confirming that the modified siRNA molecule is less immunostimulatory by contacting the modified siRNA molecule with a mammalian responder cell under conditions suitable for the responder cell to produce a detectable immune response.

In a related aspect, the present invention provides a method for identifying and modifying an immunostimulatory siRNA that silences CSN5 gene expression, the method comprising:
 (a) contacting an unmodified siRNA sequence capable of silencing CSN5 gene expression with a mammalian responder cell under conditions suitable for the responder cell to produce a detectable immune response;
 (b) identifying the unmodified siRNA sequence as an immunostimulatory siRNA by the presence of a detectable immune response in the responder cell; and
 (c) modifying the unmodified siRNA sequence by substituting one or more nucleotides with modified nucleotides, thereby generating a modified siRNA molecule that is less immunostimulatory than the unmodified siRNA sequence.

In one embodiment, the modified siRNA molecule comprises modified nucleotides selected from the group consisting of 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In a preferred embodiment, the modified siRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

Typically, two, three, four, five, six, seven, or more of the nucleotides in the unmodified siRNA sequence are substituted with modified nucleotides. In some embodiments, less than about 30%, 25%, 20%, 15%, 10%, or 5% of the nucleotides in the double-stranded region of the unmodified siRNA sequence are substituted with modified nucleotides. In other embodiments, from about 10% to about 20% of the nucleotides in the double-stranded region of the unmodified siRNA sequence are substituted with modified nucleotides.

In certain instances, the modified siRNA molecule is at least about 70% less immunostimulatory than the unmodified siRNA sequence. In certain other instances, the modified siRNA molecule has an $IC_{50}$ that is less than or equal to ten-fold that of the unmodified siRNA sequence.

In some embodiments, the mammalian responder cell is a peripheral blood mononuclear cell or dendritic cell. In other embodiments, the detectable immune response comprises production of a cytokine or growth factor selected from the group consisting of TNF-α, IFN-α, IFN-β, IFN-γ, IL-6, IL-12, and combinations thereof. In further embodiments, the detectable immune response comprises induction of interferon-induced protein with tetratricopeptide repeats 1 (IFIT1) mRNA.

In further aspects, the present invention provides compositions comprising asymmetrical interfering RNA (aiRNA) molecules that target CSN5 gene expression and methods of using such compositions to silence CSN5 gene expression.

In one embodiment, the aiRNA molecule comprises a double-stranded (duplex) region of about 10 to about 25 (base paired) nucleotides in length, wherein the aiRNA molecule comprises an antisense strand comprising 5' and 3' overhangs, and wherein the aiRNA molecule is capable of silencing CSN5 gene expression.

In certain instances, the aiRNA molecule comprises a double-stranded (duplex) region of about 12-20, 12-19, 12-18, 13-17, or 14-17 (base paired) nucleotides in length, more typically 12, 13, 14, 15, 16, 17, 18, 19, or 20 (base paired) nucleotides in length. In certain other instances, the 5' and 3' overhangs on the antisense strand comprise sequences that are complementary to the target CSN5 mRNA, and may optionally further comprise nontargeting sequences. In some embodiments, each of the 5' and 3' overhangs on the antisense strand comprises or consists of one, two, three, four, five, six, seven, or more nucleotides. In other embodiments, the antisense strand comprises or consists of a sequence that is at least about 80%, 85%, 90%, 95%, 96%, 97%, 98%, 99%, or 100% complementary to a target CSN5 sequence or a portion thereof.

In further embodiments, the aiRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof. In a preferred embodiment, the aiRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

In related aspects, the present invention provides compositions comprising microRNA (miRNA) molecules that target CSN5 gene expression and methods of using such compositions to silence CSN5 gene expression.

In one embodiment, the miRNA molecule comprises about 15 to about 60 nucleotides in length, wherein the miRNA molecule is capable of silencing CSN5 gene expression.

In certain instances, the miRNA molecule comprises about 15-50, 15-40, or 15-30 nucleotides in length, more typically about 15-25 or 19-25 nucleotides in length, and are preferably about 20-24, 21-22, or 21-23 nucleotides in length. In a preferred embodiment, the miRNA molecule is a mature miRNA molecule targeting CSN5 mRNA.

In some embodiments, the miRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof. In a preferred embodiment, the miRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

IV. Nucleic Acids

In certain embodiments, lipid particles of the present invention are associated with a nucleic acid, resulting in a nucleic acid-lipid particle (e.g., SNALP). In some embodiments, the nucleic acid is fully encapsulated in the nucleic acid-lipid particle. As used herein, the term "nucleic acid" includes any oligonucleotide or polynucleotide, with fragments containing up to 60 nucleotides generally termed oligonucleotides, and longer fragments termed polynucleotides. In particular embodiments, oligonucletoides of the invention are from about 15 to about 60 nucleotides in length. Nucleic acid may be administered alone in the nucleic acid-lipid particles of the invention, or in combination (e.g., co-administered) with one or more therapeutic peptides, polypeptides, or small organic molecules or compounds (e.g., conventional drugs) suitable for treating a cell proliferative disorder such as cancer.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a nucleic acid-lipid particle according to the invention includes any form of nucleic acid that is known. The nucleic acids used herein can be single-stranded DNA or RNA, or double-stranded DNA or RNA, or DNA-RNA hybrids. Examples of double-stranded DNA include, e.g., structural genes, genes including control and termination regions, and self-replicating systems such as viral or plasmid DNA. Examples of double-stranded RNA include, e.g., siRNA and other RNAi agents such as aiRNA and pre-miRNA. Single-stranded nucleic acids include, e.g., antisense oligonucleotides, ribozymes, mature miRNA, and triplex-forming oligonucleotides.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

A. siRNA

The unmodified and modified siRNA molecules of the invention are capable of silencing CSN5 gene expression, e.g., to inhibit cancer cell proliferation and/or to induce cancer cell death, and are typically about 15 to 60 nucleotides in length. The modified siRNA molecules are generally less immunostimulatory than a corresponding unmodified siRNA sequence and retain RNAi activity against the target CSN5 sequence. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. In preferred embodiments, one or more of the uridine and/or guanosine nucleotides are modified. The modified nucleotides can be present in one strand (i.e., sense or antisense) or both strands of the siRNA. The siRNA sequences may have overhangs (e.g., 3' or 5' overhangs as described in Elbashir et al., Genes Dev., 15:188 (2001) or Nykänen et al., Cell, 107:309 (2001)), or may lack overhangs (i.e., have blunt ends).

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides.

In some embodiments, less than about 25% (e.g., less than about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%) of the nucleotides in the double-stranded region of the siRNA comprise modified nucleotides.

In other embodiments, from about 1% to about 25% (e.g., from about 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, etc.) or from about 1% to about 20% (e.g., from about 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, etc.) of the nucleotides in the double-stranded region of the siRNA comprise modified nucleotides.

In further embodiments, e.g., when one or both strands of the siRNA are selectively modified at uridine and/or guanosine nucleotides, the resulting modified siRNA can comprise less than about 30% modified nucleotides (e.g., less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% modified nucleotides) or from about 1% to about 30% modified nucleotides (e.g., from about 1%-30%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, or 29%-30% modified nucleotides).

1. Selection of siRNA Sequences

Suitable siRNA sequences can be identified using any means known in the art. Typically, the methods described in Elbashir et al., Nature, 411:494-498 (2001) and Elbashir et al., EMBO J., 20:6877-6888 (2001) are combined with rational design rules set forth in Reynolds et al., Nature Biotech., 22(3):326-330 (2004).

Generally, the nucleotide sequence 3' of the AUG start codon of a transcript from the target gene of interest is scanned for dinucleotide sequences (e.g., AA, NA, CC, GG, or UU, wherein N=C, G, or U) (see, e.g., Elbashir et al., EMBO J., 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing ° efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://boz094.ust.hk/RNAi/siRNA. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell*, 115:209-216 (2003); and Schwarz et al., *Cell*, 115:199-208 (2003). In other embodiments, potential siRNA sequences may be further analyzed based on secondary structure at the target site as described in, e.g., Luo et al., *Biophys. Res. Commun.*, 318: 303-310 (2004). For example, secondary structure at the target site can be modeled using the Mfold algorithm (available at http://www.bioinfo.rpi.edu/applications/mfold/rna/form1.cgi) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.*, 255:4980-4983 (1980)); enzyme-linked immunosorbent assays (ELISA) as described, for example, by Raines et al., *J. Biol. Chem.*, 257:5154-5160 (1982); immunocytochemical techniques, including the use of fluorochromes (Brooks et al., *Clin. Exp. Immunol.*, 39:477 (1980)); and neutralization of activity (Bowen-Pope et al., *Proc. Natl. Acad. Sci. USA*, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., *Mol. Ther.*, 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., *Nature*, 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

2. Generating siRNA Molecules siRNA can be provided in several forms including, e.g., as one or more isolated small-interfering RNA (siRNA)

duplexes, as longer double-stranded RNA (dsRNA), or siRNA or dsRNA transcribed from a transcriptional cassette in a DNA plasmid. The siRNA sequences may have overhangs (e.g., 3' or 5' overhangs as described in Elbashir et al., *Genes Dev.*, 15:188 (2001) or Nykänen et al., *Cell,* 107:309 (2001), or may lack overhangs (i.e., to have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 mol scale protocol. Alternatively, syntheses at the 0.2 μmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

3. Modifying siRNA Sequences

In certain aspects, the siRNA molecules of the present invention comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets the CSN5 gene can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence CSN5 gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure,* Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.,* 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.,* 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides; 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-, phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

B. aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.*, 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, the aiRNA molecules of the present invention may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, the aiRNA molecule of the present invention comprises an antisense strand which corresponds to the antisense strand of an siRNA molecule, e.g., one of the siRNA molecules described herein which displays CSN5 silencing activity. In some instances, aiRNAs targeting CSN5 mRNA are administered using a carrier system described herein such as a nucleic acid-lipid particle (e.g., SNALP). In a preferred embodiment, the nucleic acid-lipid particle comprises: (a) one or more aiRNA molecules targeting CSN5 mRNA; (b) a cationic lipid (e.g., DLinDMA and/or XTC2); and (c) a non-cationic lipid (e.g., DSPC, DPPC, DSPE, and/or cholesterol). In certain instances, the nucleic acid-lipid particle may further comprise a conjugated lipid that prevents aggregation of particles (e.g., a PEG-lipid conjugate such as PEG-DAA).

C. miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNAs is described, e.g., in Lagos-Quintana et al., *Science,* 294:853-858; Lau et al., *Science,* 294:858-862; and Lee et al., *Science,* 294:862-864.

The genes encoding miRNAs are much longer than the processed mature miRNA molecule. miRNAs are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature,* 432:231-235 (2004)). These pre-miRNAs are then processed to mature miRNAs in the cytoplasm by interaction with the endonuclease Dicer, which also initiates the formation of the RNA-induced silencing complex (RISC) (Bernstein et al., *Nature,* 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.,* 16:530-535 (2006)). The remaining strand, known as the anti-guide or passenger strand, is degraded as a RISC complex substrate (Gregory et al., *Cell,* 123:631-640 (2005)). After integration into the active RISC complex, miRNAs base pair with their complementary mRNA molecules and induce target mRNA degradation and/or translational silencing.

Mammalian miRNAs are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNAs may also target methylation of genomic sites which correspond to targeted mRNAs. Generally, miRNAs function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, the miRNA molecules described herein may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In some embodiments, miRNAs targeting CSN5 mRNA are administered using a carrier system described herein such as a nucleic acid-lipid particle (e.g., SNALP). In a preferred embodiment, the nucleic acid-lipid particle comprises: (a) one or more miRNA molecules targeting CSN5 mRNA; (b) a cationic lipid (e.g., DLinDMA and/or XTC2); and (c) a non-cationic lipid (e.g., DSPC, DPPC, DSPE, and/or cholesterol). In certain instances, the nucleic acid-lipid particle may further comprise a conjugated lipid that prevents aggregation of particles (e.g., a PEG-lipid conjugate such as PEG-DAA).

In other embodiments, one or more agents that block the activity of a miRNA targeting CSN5 mRNA are administered using a carrier system described herein (e.g., a nucleic acid-lipid particle). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target mRNA.

V. Carrier Systems Containing Nucleic Acids

In one aspect, the present invention provides carrier systems containing one or more nucleic acids described herein, e.g., unmodified or modified interfering RNA such as siRNA, aiRNA, or miRNA. In some embodiments, the carrier system is a lipid-based carrier system such as a stable nucleic acid-lipid particle (e.g., SNALP or SPLP), a cationic lipid or liposome nucleic acid complex (i.e., lipoplex), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system is a nucleic acid-lipid particle such as a SNALP or SPLP. One skilled in the art will appreciate that the nucleic acids (e.g., interfering RNA) of the present invention can also be delivered as a naked molecule.

A. Stable Nucleic Acid-Lipid Particles

In preferred embodiments, the nucleic acid-lipid particles of the present invention are serum-stable nucleic acid-lipid particles (SNALP) which comprise an interfering RNA (e.g., siRNA, aiRNA, and/or miRNA), a cationic lipid (e.g., a cationic lipid of Formulas I, II, and/or III), a non-cationic lipid (e.g., cholesterol alone or mixtures of one or more phospholipids and cholesterol), and optionally a conjugated lipid that inhibits aggregation of the particles (e.g., one or more PEG-lipid conjugates). The SNALP may comprise at least 1, 2, 3, 4, 5, 6, 7, 8, 9, 10, or more unmodified and/or modified interfering RNA molecules.

The SNALP of the present invention typically have a mean diameter of from about 40 nm to about 150 nm, from about 50 nm to about 150 nm, from about 60 nm to about 130 nm, from about 70 nm to about 110 nm, or from about 70 to about 90 nm, and are substantially nontoxic. In addition, the nucleic acids are resistant in aqueous solution to degradation with a nuclease when present in the nucleic acid-lipid particles. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are herein incorporated by reference in their entirety for all purposes.

1. Cationic Lipids

Any of a variety of cationic lipids may be used in the nucleic acid-lipid particles of the invention (e.g., SNALP), either alone or in combination with one or more other cationic lipid species or non-cationic lipid species.

Cationic lipids which are useful in the present invention can be any of a number of lipid species which carry a net positive charge at physiological pH. Such lipids include, but are not limited to, N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl) cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethy-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3.beta.-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-Dilinoleylcarbamyl-3-dimethylaminopropane (DLincarbDAP), 1,2-Dilinoleoylcarbamyl-3-dimethylaminopropane (DLinCDAP), and mixtures thereof. A number of these lipids and related analogs have been described in U.S. Patent Publication Nos. 20060083780 and 20060240554; U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids are available and can be used in the present invention. These include, e.g., LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

Additionally, cationic lipids of Formula I having the following structures are useful in the present invention.

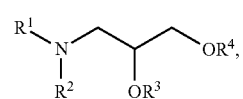

(I)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradectrienyl ($C_{14}$) and $R^4$ is linoleyl ($C_{18}$). In a preferred embodiment, the cationic lipid of Formula I is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl. In particularly preferred embodiments, the cationic lipid of Formula I is 1,2-dilinoleyloxy-N,N-dimethylaminopropane (DLinDMA) or 1,2-dilinolenyloxy-N,N-dimethylaminopropane (DLenDMA).

Furthermore, cationic lipids of Formula II having the following structures are useful in the present invention.

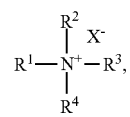

(II)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradectrienyl ($C_{14}$) and $R^4$ is linoleyl ($C_{18}$). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

Moreover, cationic lipids of Formula III having the following structures (or salts thereof) are useful in the present invention.

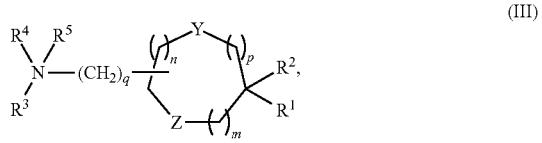

(III)

Wherein $R^1$ and $R^2$ are either the same or different and independently optionally substituted $C_{12}$-$C_{24}$ alkyl, optionally substituted $C_{12}$-$C_{24}$ alkenyl, optionally substituted $C_{12}$-$C_{24}$ alkynyl, or optionally substituted $C_{12}$-$C_{24}$ acyl; $R^3$ and $R^4$ are either the same or different and independently optionally substituted $C_1$-$C_6$ alkyl, optionally substituted $C_1$-$C_6$ alkenyl, or optionally substituted $C_1$-$C_6$ alkynyl or $R^3$ and $R^4$ may join to form an optionally substituted heterocyclic ring of 4 to 6 carbon atoms and 1 or 2 heteroatoms chosen from nitrogen and oxygen; $R^5$ is either absent or hydrogen or $C_1$-$C_6$ alkyl to provide a quaternary amine; m, n, and p are either the same or different and independently either 0 or 1 with the proviso that m, n, and p are not simultaneously 0; q is 0, 1, 2, 3, or 4; and Y and Z are either the same or different and independently O, S, or NH.

In some embodiments, the cationic lipid of Formula III is 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ),2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ),3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), or mixtures thereof. In preferred embodiments, the cationic lipid of Formula III is DLin-K-C2-DMA (XTC2).

In some embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 55 mol % to about 65 mol % of the total lipid present in the particle.

In other embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % of the total lipid present in the particle.

Additional percentages and ranges of cationic lipids suitable for use in the nucleic acid-lipid particles of the invention are described in Section III above.

It will be readily apparent to one of skill in the art that depending on the intended use of the particles, the proportions of the components can be varied and the delivery efficiency of a particular formulation can be measured using, e.g., an endosomal release parameter (ERP) assay.

2. Non-Cationic Lipids

The non-cationic lipids used in the nucleic acid-lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lyso-phosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof such as cholestanol, cholestanone, cholestenone, coprostanol, cholesteryl-2'-hydroxyethyl ether, cholesteryl-4'-hydroxybutyl ether, and mixtures thereof.

In some embodiments, the non-cationic lipid present in the nucleic acid-lipid particles comprises or consists of cholesterol or a derivative thereof, e.g., a phospholipid-free formulation. In other embodiments, the non-cationic lipid present in the nucleic acid-lipid particles comprises or consists of one or more phospholipids, e.g., a cholesterol-free formulation. In further embodiments, the non-cationic lipid present in the nucleic acid-lipid particles comprises or consists of a mixture of one or more phospholipids and cholesterol or a derivative thereof.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 13 mol % to about 49.5 mol %, from about 20 mol % to about 45 mol %, from about 25 mol % to about 45 mol %, from about 30 mol % to about 45 mol %, from about 35 mol % to about 45 mol %, from about 20 mol % to about 40 mol %, from about 25 mol % to about 40 mol %, or from about 30 mol % to about 40 mol % of the total lipid present in the particle.

In certain embodiments, the cholesterol present in phospholipid-free nucleic acid-lipid particles comprises from about 30 mol % to about 45 mol %, from about 30 mol % to about 40 mol %, from about 35 mol % to about 45 mol %, or from about 35 mol % to about 40 mol % of the total lipid present in the particle. As a non-limiting example, such particles may comprise cholesterol at about 37 mol % of the total lipid present in the particle.

In certain other embodiments, the cholesterol present in nucleic acid-lipid particles containing a mixture of phospholipid and cholesterol comprises from about 30 mol % to about 40 mol %, from about 30 mol % to about 35 mol %, or from about 35 mol % to about 40 mol % of the total lipid present in the particle. As a non-limiting example, such particles may comprise cholesterol at about 34 mol % of the total lipid present in the particle.

In embodiments where the nucleic acid-lipid particles contain a mixture of phospholipid and cholesterol or a cholesterol derivative, the mixture may comprise up to about 40, 45, 50, 55, or 60 mol % of the total lipid present in the particle. In certain instances, the phospholipid component in the mixture may comprise from about 2 mol % to about 12 mol %, from about 4 mol % to about 10 mol %, from about 5 mol % to about 10 mol %, from about 5 mol % to about 9 mol %, or from about 6 mol % to about 8 mol % of the total lipid present in the particle. As a non-limiting example, a nucleic acid-lipid particle comprising a mixture of phospholipid and cholesterol may comprise a phospholipid such as DPPC or DSPC at about 7 mol % (e.g., in a mixture with about 34 mol % cholesterol) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) of the total lipid present in the particle.

Additional percentages and ranges of non-cationic lipids suitable for use in the nucleic acid-lipid particles of the invention are described in Section III above.

3. Lipid Conjugate

In addition to cationic and non-cationic lipids, the nucleic acid-lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes. Additional PEG-lipids include, without limitation, PEG-C-DOMG, 2 KPEG-DMG, and a mixture thereof.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" refers to, without limitation, compounds described in U.S. Pat. Nos. 6,320,017 and 6,586,559, the disclosures of which are herein incorporated by reference in their entirety for all purposes. These compounds include a compound having the formula:

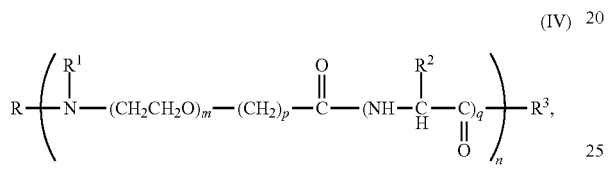
(IV)

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" refers to a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc. Diacylglycerols have the following general formula:

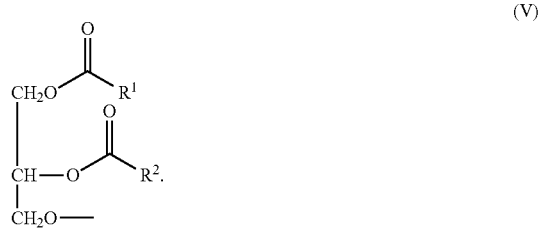
(V)

The term "dialkyloxypropyl" refers to a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

(VI)

In a preferred embodiment, the PEG-lipid is a PEG-DAA conjugate having the following formula:

(VII)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VII above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons or about 750 daltons. The PEG can be optionally substituted with alkyl, alkoxy, acyl, or aryl. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

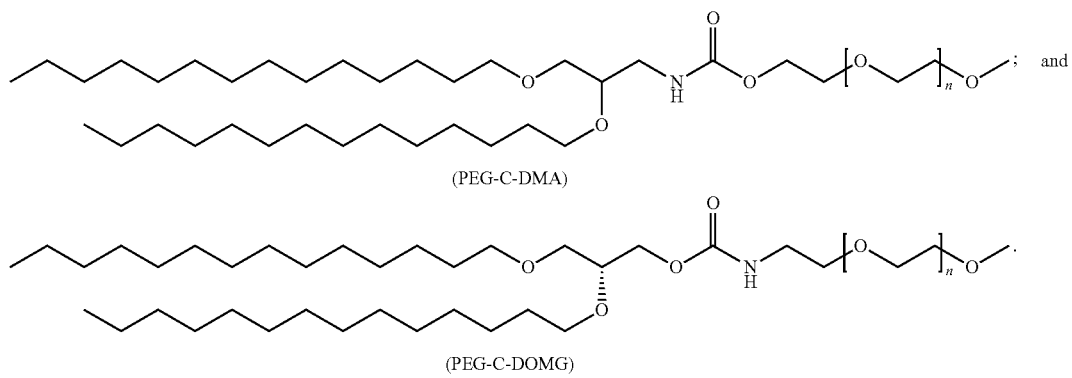

(PEG-C-DMA)

(PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a dilauryloxypropyl ($C_{12}$)-PEG conjugate, dimyristyloxypropyl ($C_{14}$)-PEG conjugate, a dipalmityloxypropyl ($C_{16}$)-PEG conjugate, or a distearyloxypropyl ($C_{18}$)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the particles (e.g., SNALP or SPLP) of the present invention can further comprise cationic poly(ethylene glycol) (PEG) lipids or CPLs (see, e.g., Chen et al., *Bioconj. Chem.*, 11:433-437 (2000)). Suitable SPLPs and SPLP-CPLs for use in the present invention, and methods of making and using SPLPs and SPLP-CPLs, are disclosed, e.g., in U.S. Pat. No. 6,852,334 and PCT Publication No. WO 00/62813, the disclosures of which are herein incorporated by reference in their entirety for all purposes.

Suitable CPLs include compounds of Formula VIII:

A-W-Y    (VIII), wherein A, W, and Y are as described below.

With reference to Formula VIII, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.5 mol % of the total lipid present in the particle.

In other embodiments, the lipid conjugate (e.g., PEG-lipid) comprises from about 0 mol % to about 20 mol %, from about 0.5 mol % to about 20 mol %, from about 1.5 mol % to about 18 mol %, from about 4 mol % to about 15 mol %, from about 5 mol % to about 12 mol %, or about 2 mol % of the total lipid present in the particle.

Additional percentages and ranges of lipid conjugates suitable for use in the nucleic acid-lipid particles of the invention are described in Section III above.

One of ordinary skill in the art will appreciate that the concentration of the lipid conjugate can be varied depending on the lipid conjugate employed and the rate at which the nucleic acid-lipid particle is to become fusogenic.

By controlling the composition and concentration of the lipid conjugate, one can control the rate at which the lipid conjugate exchanges out of the nucleic acid-lipid particle and, in turn, the rate at which the nucleic acid-lipid particle becomes fusogenic. For instance, when a PEG-phosphatidylethanolamine conjugate or a PEG-ceramide conjugate is used as the lipid conjugate, the rate at which the nucleic acid-lipid particle becomes fusogenic can be varied, for example, by varying the concentration of the lipid conjugate, by varying the molecular weight of the PEG, or by varying the chain length and degree of saturation of the acyl chain groups on the phosphatidylethanolamine or the ceramide. In addition, other variables including, for example, pH, temperature, ionic strength, etc. can be used to vary and/or control the rate at which the nucleic acid-lipid particle becomes fusogenic. Other methods which can be used to control the rate at which the nucleic acid-lipid particle becomes fusogenic will become apparent to those of skill in the art upon reading this disclosure.

B. Additional Carrier Systems

Non-limiting examples of additional lipid-based carrier systems suitable for use in the present invention include lipoplexes (see, e.g., U.S. Patent Publication No. 20030203865; and Zhang et al., *J. Control Release*, 100:165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use in the present invention include, but are not limited to, cationic polymer-nucleic acid complexes (i.e., polyplexes). To form a polyplex, a nucleic acid (e.g., interfering RNA) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid (e.g., interfering RNA) complexed with a cationic polymer such as polyethylenimine (PEI) (see, e.g., U.S. Pat. No. 6,013,240; commercially available from Qbiogene, Inc. (Carlsbad, Calif.) as In vivo jetPEI™, a linear form of PEI), polypropylenimine (PPI), polyvinylpyrrolidone (PVP), poly-L-lysine (PLL), diethylaminoethyl (DEAE)-dextran, poly(β-amino ester) (PAE) polymers (see, e.g., Lynn et al, *J. Am. Chem. Soc.*, 123:8155-8156 (2001)), chitosan, polyamidoamine (PAMAM) dendrimers (see, e.g., Kukowska-Latallo et al., *Proc. Natl. Acad. Sci. USA*, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No., WO/9602655; PCT Publication No. WO95/21931; Zhang et al., *J. Control Release*, 100:165-180 (2004); and Tiera et al., *Curr. Gene Ther.*, 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly(β-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, the nucleic acid (e.g., interfering RNA) may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, the nucleic acid (e.g., interfering RNA) may be complexed with a peptide or polypeptide. An example of a protein-based carrier system includes, but is not limited to, the cationic oligopeptide-nucleic acid complex described in PCT Publication No. WO95/21931.

The disclosures of the above-described patent documents and other publications are herein incorporated by reference in their entirety for all purposes.

V. Preparation of Nucleic Acid-Lipid Particles

The serum-stable nucleic acid-lipid particles of the present invention, in which a nucleic acid such as an interfering RNA is encapsulated in a lipid bilayer and is protected from degradation, can be formed by any method known in the art including, but not limited to, a continuous mixing method or a direct dilution process.

In preferred embodiments, the cationic lipids are lipids of Formula I, II, and III, or combinations thereof. In other preferred embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, or combinations thereof.

In certain embodiments, the present invention provides for nucleic acid-lipid particles produced via a continuous mixing method, e.g., a process that includes providing an aqueous solution comprising a nucleic acid such as an interfering RNA in a first reservoir, providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., interfering RNA). This process and the apparatus for carrying this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 40 nm to about 150 nm, from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In another embodiment, the present invention provides for nucleic acid-lipid particles produced via a direct dilution process that includes forming a liposome solution and immediately and directly introducing the liposome solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of liposome solution introduced thereto. As a non-limiting example, a liposome solution in 45% ethanol when introduced into the collection vessel containing an equal volume of dilution buffer will advantageously yield smaller particles.

In yet another embodiment, the present invention provides for nucleic acid-lipid particles produced via a direct dilution process in which a third reservoir containing dilution buffer is fluidly coupled to a second mixing region. In this embodiment, the liposome solution formed in a first mixing region is immediately and directly mixed with dilution buffer in the second mixing region. In preferred aspects, the second mixing region includes a T-connector arranged so that the liposome solution and the dilution buffer flows meet as opposing 180° flows; however, connectors providing shallower angles can be used, e.g., from about 27° to about 180°. A pump mechanism delivers a controllable flow of buffer to the second mixing region. In one aspect, the flow rate of dilution buffer provided to the second mixing region is controlled to be substantially equal to the flow rate of liposome solution introduced thereto from the first mixing region. This embodiment advantageously allows for more control of the flow of dilution buffer mixing with the liposome solution in the second mixing region, and therefore also the concentration of liposome solution in buffer throughout the second mixing process. Such control of the dilution buffer flow rate advantageously allows for small particle size formation at reduced concentrations.

These processes and the apparatuses for carrying out these direct dilution processes are described in detail in U.S. Patent Publication No. 20070042031, the disclosure of which is herein incorporated by reference in its entirety for all purposes.

The nucleic acid-lipid particles formed using the direct dilution process typically have a size of from about 40 nm to about 150 nm, from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

If needed, the nucleic acid-lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids in the particles are precondensed as described in, e.g., U.S. patent application Ser. No. 09/744,103, the disclosure of which is herein incorporated by reference in its entirety for all purposes.

In other embodiments, the methods will further comprise adding non-lipid polycations which are useful to effect the lipofection of cells using the present compositions. Examples of suitable non-lipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle will range from about 0.01 to about 0.2, from about 0.02 to about 0.1, from about 0.03 to about 0.1, or from about 0.01 to about 0.08. The ratio of the starting materials also falls within this range. In other embodiments, the particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), about 5 (5:1), 6 (6:1), 7 (7:1), 8 (8:1), 9 (9:1), 10 (10:1), 11 (11:1), 12(12:1), 13 (13:1), 14 (14:1), or 15 (15:1). The ratio of the starting materials also falls within this range.

As previously discussed, the conjugated lipid may further include a CPL. A variety of general methods for making SNALP-CPLs (CPL-containing SNALP) are discussed herein. Two general techniques include "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPL, are taught, for example, in U.S. Pat. Nos. 5,705,385; 6,586,410; 5,981, 501; 6,534,484; and 6,852,334; U.S. Patent Publication No. 20020072121; and PCT Publication No. WO 00/62813, the disclosures of which are herein incorporated by reference in their entirety for all purposes.

VI. Kits

The present invention also provides nucleic acid-lipid particles (e.g., SNALP) in kit form. The kit may comprise a container which is compartmentalized for holding the various elements of the particles (e.g., the nucleic acids such as interfering RNA and the individual lipid components of the particles). In some embodiments, the kit may further comprise an endosomal membrane destabilizer (e.g., calcium ions). The kit typically contains the particle compositions of the present invention, preferably in dehydrated form, with instructions for their rehydration and administration.

As explained herein, the nucleic acid-lipid particles of the invention can be tailored to preferentially target particular tissues, organs, or tumors of interest. In certain instances, preferential targeting of SNALP may be carried out by controlling the composition of the SNALP itself. For example, it has been found that the 1:57 PEG-cDSA SNALP formulation can be used to preferentially target tumors outside of the liver, whereas the 1:57 PEG-cDMA SNALP formulation can be used to preferentially target the liver (including liver tumors). The tumor targeting abilities of these SNALP formulations is described in U.S. Provisional Application No. 61/045,228, filed Apr. 15, 2008, the disclosure of which is herein incorporated by reference in its entirety for all purposes.

In certain other instances, it may be desirable to have a targeting moiety attached to the surface of the particle to further enhance the targeting of the SNALP. Methods of attaching targeting moieties (e.g., antibodies, proteins, etc.) to lipids (such as those used in the present particles) are known to those of skill in the art.

VII. Administration of Nucleic Acid-Lipid Particles

Once formed, the serum-stable nucleic acid-lipid particles (SNALP) of the present invention are useful for the introduction of nucleic acids (e.g., interfering RNA) into cells. Accordingly, the present invention also provides methods for introducing a nucleic acid (e.g., interfering RNA) into a cell. The methods are carried out in vitro or in vivo by first forming the particles as described above and then contacting the particles with the cells for a period of time sufficient for delivery of the nucleic acid to the cells to occur.

The nucleic acid-lipid particles of the invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

The nucleic acid-lipid particles of the invention can be administered either alone or in a mixture with a pharmaceutically-acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically-acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human.

The pharmaceutically-acceptable carrier is generally added following particle formation. Thus, after the particle is formed, the particle can be diluted into pharmaceutically-acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

A. In vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated nucleic acid-lipid particles that protect the nucleic acid from nuclease degradation in serum, are nonimmunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the nucleic acid-lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the nucleic acid-lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the nucleic acid-lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged nucleic acid (e.g., interfering RNA) suspended in diluents such as water, saline, or PEG 400; (b) capsules, sachets, or tablets, each containing a predetermined amount of a nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a nucleic acid (e.g., interfering RNA) in a flavor, e.g., sucrose, as well as pastilles comprising the nucleic acid in an inert base, such as gelatin and glycerin or sucrose and acacia emulsions, gels, and the like containing, in addition to the nucleic acid, carriers known in the art.

In another example of their use, nucleic acid-lipid particles can be incorporated into a broad range of topical dosage forms. For instance, a suspension containing the particles can be formulated and administered as gels, oils, emulsions, topical creams, pastes, ointments, lotions, foams, mousses, and the like.

When preparing pharmaceutical preparations of the nucleic acid-lipid particles of the invention, it is preferable to use quantities of the particles which have been purified to reduce or eliminate empty particles or particles with nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of nucleic acid (e.g., interfering RNA) to lipid, the particular nucleic acid used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

In addition to its utility in silencing CSN5 gene expression for therapeutic purposes, the nucleic acids (e.g., interfering RNA such as siRNA) described herein are also useful in research and development applications as well as diagnostic, prophylactic, prognostic, clinical, and other healthcare applications.

B. In vitro Administration

For in vitro applications, the delivery of nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the nucleic acid-lipid particles, when carried out in vitro, takes place in a biologically compatible medium. The concentration of particles varies widely depending on the particular application, but is generally between about 1 µmol and about 10 mmol. Treatment of the cells with the nucleic acid-lipid particles is generally carried out at physiological temperatures (about 37° C.) for periods of time of from about 1 to 48 hours, preferably of from about 2 to 4 hours.

In one group of preferred embodiments, a nucleic acid-lipid particle suspension is added to 60-80% confluent plated cells having a cell density of from about $10^3$ to about $10^5$ cells/ml, more preferably about $2 \times 10^4$ cells/ml. The concentration of the suspension added to the cells is preferably of from about 0.01 to 0.2 µg/ml, more preferably about 0.1 µg/ml.

Using an Endosomal Release Parameter (ERP) assay, the delivery efficiency of the nucleic acid-lipid particle (e.g., SNALP) or other lipid-based carrier system can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of particles based on their relative effect on binding/uptake or fusion with/destabilization of the endosomal membrane. This assay allows one to determine quantitatively how each component of the particle or other lipid-based carrier system affects delivery efficiency, thereby optimizing the particles or other lipid-based carrier systems. Usually, an ERP assay measures expression of a reporter protein (e.g., luciferase, galactosidase, green fluorescent protein (GFP), etc.), and in some instances, a particle formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various particles or other lipid-based formulations, one can readily determine the optimized system, e.g., the SNALP or other lipid-based formulation that has the greatest uptake in the cell.

C. Cells for Delivery of Interfering RNA

The compositions and methods of the present invention are used to treat a wide variety of cell types, in vivo and in vitro. Suitable cells include, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like. In preferred embodiments, a nucleic acid such as an interfering RNA (e.g., siRNA) is delivered to cancer cells such as, e.g., liver cancer cells, lung cancer cells, colon cancer cells, rectal cancer cells, anal cancer cells, bile duct cancer cells, small intestine cancer cells, stomach (gastric) cancer cells, esophageal cancer cells, gallbladder cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In vivo delivery of nucleic acid-lipid particles encapsulating an interfering RNA (e.g., siRNA) is suited for targeting cells of any cell type. The methods and compositions can be employed with cells of a wide variety of vertebrates, including mammals, such as, e.g., canines, felines, equines, bovines, ovines, caprines, rodents (e.g., mice, rats, and guinea pigs), lagomorphs, swine, and primates (e.g. monkeys, chimpanzees, and humans).

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

D. Detection of SNALP

In some embodiments, the nucleic acid-lipid particles are detectable in the subject at about 1, 2, 3, 4, 5, 6, 7, 8 or more hours. In other embodiments, the nucleic acid-lipid particles are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of an interfering RNA (e.g., siRNA) sequence, detection of the target sequence of interest (i.e., by detecting expression or reduced expression of the sequence of interest), or a combination thereof.

1. Detection of Particles

Nucleic acid-lipid particles can be detected using any methods known in the art. For example, a label can be coupled directly or indirectly to a component of the SNALP using methods well-known in the art. A wide variety of labels can be used, with the choice of label depending on sensitivity required, ease of conjugation with the SNALP component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA such as siRNA) are detected and quantified herein by any of a number of means well-known to those of skill in the art. The detection of nucleic acids proceeds by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), C&EN 36; The *Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241: 1077 (1988); Van Brunt, *Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of ploynucleotides, where necessary, is typically performed by either native acrylamide gel electrophoresis or by anion exchange HPLC as described in Pearson et al., *J. Chrom.*, 255:137 149 (1983). The sequence of the synthetic poluyucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

VIII. Combination Therapy

In some embodiments, the present invention provides methods for treating a cell proliferative disorder such as cancer (e.g., liver cancer) by administering an interfering RNA targeting the CSN5 gene (e.g., an siRNA using a suitable carrier system) in combination with a chemotherapy drug. The methods can be carried out in vitro using standard tissue culture techniques or in vivo by administering the interfering RNA and chemotherapy drug as described herein or using any means known in the art. In preferred embodiments, this combination of therapeutic agents is delivered to a cancer cell in a mammal such as a human.

In certain aspects, a patient about to begin chemotherapy is first pretreated with a suitable dose of one or more nucleic acid-lipid particles (e.g., SNALP) containing CSN5 interfering RNA (e.g., siRNA). The patient can be pretreated with a suitable dose of one or more nucleic acid-lipid particles at any reasonable time prior to chemotherapy drug administration. As non-limiting examples, the dose of one or more nucleic acid-lipid particles can be administered about 96, 84, 72, 60, 48, 36, 24, 23, 22, 21, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, or 0.1 hours, or any interval thereof, before chemotherapy drug administration.

Additionally, a patient about to begin chemotherapy can be pretreated with more than one dose of nucleic acid-lipid particles (e.g., SNALP) containing CSN5 interfering RNA (e.g., siRNA) at different times before chemotherapy drug administration. As such, the methods of the present invention can further comprise administering a second dose of nucleic acid-lipid particles prior to chemotherapy drug administration. In certain instances, the nucleic acid-lipid particles of the first dose are the same as the nucleic acid-lipid particles of the second dose. In certain other instances, the nucleic acid-lipid particles of the first dose are different from the nucleic acid-lipid particles of the second dose. Preferably, the two pretreatment doses use the same nucleic acid-lipid particles, e.g., SNALP containing the same CSN5 interfering RNA sequence. One skilled in the art will appreciate that the second dose of nucleic acid-lipid particles can occur at any reasonable time following the first dose. As a non-limiting example, if the first dose was administered about 12 hours before chemotherapy drug administration, the second dose can be administered about 11, 10, 9, 8, 7, 6, 5, 4, 3, 2, 1, 0.9, 0.8, 0.7, 0.6, 0.5, 0.4, 0.3, 0.2, or 0.1 hours, or any interval thereof, before chemotherapy drug administration. One skilled in the art will also appreciate that the second dose of nucleic acid-lipid particles can be the same or a different dose. In additional embodiments of the present invention, the patient can be pretreated with a third, fourth, fifth, sixth, seventh, eighth, ninth, tenth, or more dose of the same or different nucleic acid-lipid particles prior to chemotherapy drug administration.

A patient can also be treated with a suitable dose of one or more nucleic acid-lipid particles (e.g., SNALP) containing CSN5 interfering RNA (e.g., siRNA) at any reasonable time during chemotherapy drug administration. As such, the methods of the present invention can further comprise administering a dose of nucleic acid-lipid particles during chemotherapy drug administration. One skilled in the art will appreciate that more than one dose of nucleic acid-lipid particles can be administered at different times during chemotherapy drug administration. As a non-limiting example, a SNALP containing an unmodified and/or modified CSN5 siRNA sequence can be administered at the beginning of chemotherapy drug administration, while chemotherapy drug administration is in progress, and/or at the end of chemotherapy drug administration. One skilled in the art will also appreciate that the pretreatment and intra-treatment (i.e., during chemotherapy drug administration) doses of nucleic acid-lipid particles can be the same or a different dose.

In addition, a patient can be treated with a suitable dose of one or more nucleic acid-lipid particles (e.g., SNALP) containing CSN5 interfering RNA (e.g., siRNA) at any reasonable time following chemotherapy drug administration. As such, the methods of the present invention can further comprise administering a dose of nucleic acid-lipid particles after chemotherapy drug administration. As non-limiting examples, the dose of one or more nucleic acid-lipid particles can be administered about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 36, 48, 60, 72, 84, 96, 108, or more hours, or any interval thereof, after chemotherapy drug administration. In certain instances, the same nucleic acid-lipid particle is used before and after chemotherapy drug administration. In certain other instances, a different nucleic acid-lipid particle is used following chemotherapy drug administration. One skilled in the art will appreciate that more than one dose of nucleic acid-lipid particles can be administered at different times following chemotherapy drug administration. One skilled in the art will also appreciate that the pretreatment and posttreatment (i.e., following chemotherapy drug administration) doses of nucleic acid-lipid particles can be the same or a different dose.

Chemotherapy drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that a chemotherapy drug is administered at the same time, just prior to, or just after the administration of a second drug or therapeutic agent (e.g., a nucleic acid-lipid particle, another chemotherapy drug, a drug useful for reducing the side-effects associated with chemotherapy, a radiotherapeutic agent, a hormonal therapeutic agent, an immunotherapeutic agent, etc.).

Non-limiting examples of chemotherapy drugs suitable for use in the present invention include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil (5-FU), azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel (taxol), docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), tyrosine kinase inhibitors (e.g., gefitinib (Iressa®), sunitinib (Sutent®; SUI 1248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), etc.), pharmaceutically acceptable salts thereof, stereoisomers thereof, derivatives thereof, analogs thereof, and combinations thereof.

The nucleic acid-lipid particles and/or chemotherapy drugs described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the nucleic acid-lipid particles and/or chemotherapy drugs described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the nucleic acid-lipid particles and/or chemotherapy drugs described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

A therapeutically effective amount of a chemotherapy drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages. One skilled in the art will appreciate that administered dosages of chemotherapy drugs will vary depending on a number of factors, including, but not limited to, the particular chemotherapy drug or set of chemotherapy drugs to be administered, the mode of administration, the type of application, the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage.

As used herein, the term "unit dosage form" refers to physically discrete units suitable as unitary dosages for human subjects and other mammals, each unit containing a predetermined quantity of a chemotherapy drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the chemotherapy drug.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with a chemotherapy drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. A chemotherapy drug can also be formulated into a suppository disposed, for example, in a polyethylene glycol (PEG) carrier.

Liquid dosage forms can be prepared by dissolving or dispersing a chemotherapy drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. A chemotherapy drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, a chemotherapy drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

IX. EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Materials and Methods siRNA: All siRNA duplexes used for in vitro studies were chemically synthesized by Ambion. For systemic delivery of siRNA in vivo, 2'OMe modified CSN5 siRNA was synthesized by Integrated DNA Technologies and then encapsulated into SNALP. Negative control siRNA molecules that do not target any endogenous transcript are used for control experimental sets. In particular, Silencer Negative Control #1 siRNA (Ambion) and SNALP-formulated βgal478 siRNA were used for in vitro and in vivo studies, respectively. The CSN5 siRNA sequences used in these studies are shown in Tables 1-2. The βgal478 siRNA sequences are as follows: Sense strand –5'-mGAAGmGCCAGACmGCmGAA-UUAdTdT-3' (SEQ ID NO:35); Antisense strand –5'-UAAU-mUCGCGmUCUGGCCmUUCdTdT-3' (SEQ ID NO:36). mU=2'OMe-uridine; mG=2'OMe-guanosine; dT=deoxythymidine.

Lipid Encapsulation of siRNA: siRNA were encapsulated into stable nucleic acid-lipid particles (SNALP) composed of the following lipids: the lipid conjugate PEG-cDMA (3-N-[(-methoxypoly(ethylene glycol)2000)carbamoyl]-1,2-dimyristyloxypropylamine); the cationic lipid DLinDMA (1,2-dilinoleyloxy-3-(N,N-dimethyl)aminopropane); the phospholipid DPPC (1,2-dipalmitoyl-sn-glycero-3-phosphocholine; Avanti Polar Lipids; Alabaster, Ala.); and synthetic cholesterol (Sigma-Aldrich Corp.; St. Louis, Mo.) in the molar ratio 1.4:57.1:7.1:34.3, respectively. In other words, siRNA were encapsulated into SNALP of the following "1:57" formulation: 1.4 mol % PEG-cDMA; 57.1 mol % DLinDMA; 7.1 mol % DPPC; and 34.3 mol % cholesterol.

Alternatively, siRNA may be encapsulated into phospholipid-free SNALP composed of the following lipids: the lipid conjugate PEG-cDMA; the cationic lipid DLinDMA; and synthetic cholesterol in the molar ratio 1.5:61.5:36.9, respectively. In other words, siRNA may be encapsulated into phospholipid-free SNALP of the following "1:62" formulation: 1.5 mol % PEG-cDMA; 61.5 mol % DLinDMA; and 36.9 mol % cholesterol.

For vehicle controls, empty particles with identical lipid composition may be formed in the absence of siRNA.

It should be understood that the 1:57 formulation and 1:62 formulation are target formulations, and that the amount of lipid (both cationic and non-cationic) present and the amount of lipid conjugate present in the formulation may vary. Typically, in the 1:57 formulation, the amount of cationic lipid will be 57 mol %±5 mol %, and the amount of lipid conjugate will be 1.5 mol %±0.5 mol %, with the balance of the 1:57 formulation being made up of non-cationic lipid (e.g., phospholipid, cholesterol, or a mixture of the two). Similarly, in the 1:62 formulation, the amount of cationic lipid will be 62 mol %±5 mol %, and the amount of lipid conjugate will be 1.5 mol %±0.5 mol %, with the balance of the 1:62 formulation being made up of the non-cationic lipid (e.g., cholesterol).

Cell culture and transfection of siRNA in vitro: The human liver cancer cell lines, Huh7 and HepG2, were purchased from American Type Culture Collection. The cells were maintained in DMEM/F-12 media (Mediatech) supplemented with 10% fetal bovine serum (Atlanta Biologicals) at 37° C. in the presence of 5% $CO_2$. To examine the phenotypic changes in the HCC cells, before the day of transfection, 25% confluency of the cells were seeded on 96-well plates in 100 μl of culture media without antibiotics. 0.2 and 0.3 μl of Lipofectamine 2000 was mixed with siRNA molecules in a volume of 50 μl Opti-MEM I (both from Invitrogen) and added to Huh7 and HepG2 cells, respectively. The cultures were exchanged with fresh media 24 h after transfection and incubated for 2-3 days further. To compare the effects of target siRNA molecules, identical quantities of NC #1 siRNA+lipids were also added to the same number of cells and assayed simultaneously. For other assays, which are needed to transfect cells in different tissue culture formats, the amounts of lipids, siRNA, cells, and medium was proportioned to the relative surface area according to the manufacturer's protocol.

Measurement of cell proliferation and apoptotic cell death: Control siRNA or target siRNA was studied for their growth inhibitory effects using the Vybrant MTT Cell Proliferation Assay (Invitrogen) as recommended by the manufacturer. The cells were measured for absorbance at 570 nm with an ELISA reader, SpectraMAX 190 (Molecular Devices). The percentage of growth inhibition of cells in each well treated with siRNA+lipids was calculated by comparing the optical density with those of untreated control, using the following formula: 1-(absorbance of an experimental well/absorbance of a sham control well)×100. After transfection of siRNA, the induction of apoptosis was measured in cells cultured in vitro by using ApoStrand ELISA Apoptosis Detection Kit (Biomol International) that detects the denatured DNA to single-stranded DNA formed in apoptotic cells, but not in the necrotic cells or in cells with DNA breaks in the absence of apoptosis.

Detection of target gene transcripts and polypeptides: After the transfection of siRNA, the change of target gene expression in mRNA level was detected with real-time quantitative RT-PCR. Total RNA preparation was carried out with Tri reagent (Molecular Research Center) according to the protocol recommended by the manufacturer. Total RNA (1 μg) was reverse transcribed by using random primers supplied in the High-Capacity cDNA Archieve Kit (Applied Biosystems). To quantify gene expression, cDNA of the CSN5 gene was amplified by using a pair of primers (forward: 5'-TCTGCT-GAAGATGGTGATGC-3' (SEQ ID NO:37); reverse: 5'-GC-CAACCTGTTTTGCATTTT-3' (SEQ ID NO:38)) synthesized by Operon, Power SYBR Green PCR Master Mix, and an ABI 7700HT PCR Machine (both from Applied Biosystems) according to the manufacturer's instruction. To normalize the amount of total RNA present in each reaction, the GAPDH gene was amplified simultaneously. All reactions were performed in triplicate.

Quantification of proteins after siRNA treatment was performed with the Western blotting method. The amount of total proteins was determined with the BCA Protein Assay Kit (Pierce). 100 μg of total protein was run on 4-20% SDS-polyacrylamide gels and transferred onto PVDF membrane (Invitrogen). The membrane was blocked by incubating with 5% milk/Tris-buffered saline plus Tween 20 (TBST) and then incubated with primary antibodies to human CSN5 (FL-334), p53 (FL-393), p21 (C-19), and p27 (F-8) (all from Santa Cruz Biotechnology). Depending on the source of antibody production, the secondary antibody of horseradish peroxidase (HRP)-conjugated anti-rabbit IgG (Pierce), anti-goat IgG (Santa Cruz), or anti-mouse IgG (Amersham) was added, and immunoreactive bands were visualized with the ECL Plus Western Blotting Detection System (GE Healthcare). The loading of equal amounts was assessed by probing the same membrane with ACTIN antibody (NeoMarker).

Mouse strains and animal care: The immunodeficient mice used in the studies were male SCID-beige, 5-6 weeks old (Charles River Laboratories). Animal housing and care were in accordance with the guidelines from the Animal Care and Use Committee at the U.S. National Cancer Institute. These studies were approved by the Institutional Review Board of the U.S. National Cancer Institute.

Generation of HCC cell lines permanently expressing luciferase: Using Lipofectamine 2000, Huh7 cells were transfected with the pGL4.17 vector (Promega) expressing firefly luciferase and the zeocin resistance gene. To enhance the expression of the luciferase gene, the β-actin promoter from the pCAGEN plasmid (Addgene) was subcloned into the multiple cloning site of pGL4.17. Cells were selected for antibiotic resistance with Geneticin (Gibco), and surviving colonies were amplified and screened for bioluminescence in complete media supplemented with 150 μg/ml D-luciferin (Biosynth) by in vitro imaging with the IVIS Imaging System (Xenogen). A suitable Huh7-1H6 clone was selected in terms of stable luminescence in vitro and used for further studies.

Systemic administration of SNALP-formulated siRNA and bioluminescence imaging (BLI) in vivo: A total number of $5\times10^5$ Huh7-luc$^+$ cells in 50 μl of PBS buffer (with Ca$^{2+}$ and Mg$^{2+}$ ions) was transplanted into the spleen of 5-6 week-old male SCID-beige mice, and 30 seconds after cell injection spleen was removed to evade tumor formations in other organs except in liver, which is induced by cell migrations through the circulatory system. Tumors were detectable from day 7 by BLI, and kept growing exponentially up to day 28. Beginning at 8 days after transplantation, mice were randomized and administered by SNALP-formulated siRNA formulations as an i.v. injection into the lateral tail vein at a dosage of 2 mg/kg. Injections were performed four times over a period of 3-5 sec with a 3-day interval. Tumor growth in the liver was monitored by BLI for 4-weeks with 3-4 day intervals, using an IVIS Imaging System (Xenogen). Images and measurements of luciferase signals were obtained and analyzed using the Living Image Software (Xenogen). Ten minutes prior to in vivo imaging, mice were anesthetized using 1-3% isoflurane (Abbott Laboratories) and received the substrate luciferin (Biosynth) at 150 mg/kg in DPBS by an i.p. injection. Regions of interest (ROI) from displayed images were drawn around the tumor sites and quantified as photons/second using the Living Image Software.

Histopathology: To confirm the presence of neoplastic cells, liver tissues were preserved with 10% formalin solution and histological examination (paraffin embedding, sectioning, and H&E staining) was performed by Histoserv.

Cytokine induction assays: Flt3-ligand derived murine dendritic cells (Flt3L DC) were generated as described by Gilliet et al. (*J. Exp. Med.*, 195:953-958) using 100 ng/ml murine Flt3-ligand (PeproTech Inc.; Rocky Hill, N.J.) supplemented media. Femurs and tibiae of female Balb/C mice were isolated and rinsed in sterile PBS. The ends of bones were cut and marrow harvested in complete media (RPMI 1640, 10% heat inactivated FBS, 1% penicillin/streptomycin, 2 mM L-glutamine, 1 mM sodium pyruvate, 25 mM HEPES, 50 μM 2-mercaptoethanol). Bone marrow cells were passed through a 70 μm strainer, centrifuged at 1000 rpm for 7 minutes, and resuspended in complete media supplemented with 100 ng/ml murine Flt3L to $2\times10^6$ cells/ml. 2 mls of cells were seeded in 6-well plates and 1 ml fresh complete media added every two or three days. On day 9 of culture, non-adherent cells were washed in complete media and plated into 96-well plates at concentrations ranging from 0.5 to $2.5\times10^5$ cells/well. CSN5 SNALP were diluted in PBS and added to Flt3L DC cultures at 5 μg/ml siRNA. Cells were incubated for 24 hours at 37° C. before supernatants were assayed for cytokines by ELISA.

Cytokine ELISA: IL-6 levels in culture supernatants of mouse Flt3L dendricytes were quantified using a sandwich ELISA kit according to manufacturer's instructions (BD Biosciences; San Jose, Calif.).

Example 2

Exemplary Unmodified and Chemically Modified siRNA Targeting CSN5

Table 1 provides a list of exemplary siRNA sequences targeting human CSN5 gene expression.

TABLE 1 siRNA sequences that target human CSN5 gene expression.

| siRNA | Target or Sense Strand Sequence (5' → 3') | SEQ ID NO. | Antisense Strand Sequence (5' → 3') | SEQ ID NO. |
|---|---|---|---|---|
| CSN5-478 (CSN5-1) | CCAUUACUUUAAGUACUGC | 1 | GCAGUACUUAAAGUAAUGG | 2 |
| CSN5-472 (CSN5-2) | GGAUCACCAUUACUUUAAG | 3 | CUUAAAGUAAUGGUGAUCC | 4 |
| CSN5-1210 (CSN5-3) | CCGAAAAUCAGAAGACAAA | 5 | UUUGUCUUCUGAUUUUCGG | 6 |

TABLE 1-continued siRNA sequences that target human CSN5 gene expression.

| siRNA | Target or Sense Strand Sequence (5' → 3') | SEQ ID NO. | Antisense Strand Sequence (5' → 3') | SEQ ID NO. |
|---|---|---|---|---|
| CSN5-215 | GAGUCUAGGUAAGAGUUUG | 7 | CAAACUCUUACCUAGACUC | 8 |
| CSN5-1284 | UGAUGUCUCAGGUUAUUAA | 9 | UUAAUAACCUGAGACAUCA | 10 |
| CSN5-655 | UGCUCAGGCUGCUGCAUAU | 11 | AUAUGCAGCAGCCUGAGCA | 12 |
| CSN5-904 | GGGCUACAAACCUCCUGAU | 13 | AUCAGGAGGUUUGUAGCCC | 14 |
| CSN5-940 | CCAGACUAUUCCACUUAAU | 15 | AUUAAGUGGAAUAGUCUGG | 16 |
| CSN5-997 | UGCCUUAGAAGUCUCAUAU | 17 | AUAUGAGACUUCUAAGGCA | 18 |
| CSN5-1022 | UCCUCUUUGGAUCGCAAAU | 19 | AUUUGCGAUCCAAAGAGGA | 20 |
| CSN5-471 | AGGAUCACCAUUACUUUAA | 21 | UUAAAGUAAUGGUGAUCCU | 22 |
| CSN5-1045 | UGAGCUGUUGUGGAAUAAA | 23 | UUUAUUCCACAACAGCUCA | 24 |
| CSN5-1437 | GCUCUGAAGUGUCCUAAAU | 25 | AUUUAGGACACUUCAGAGC | 26 |

The number after "CSN5" in Table 1 refers to the nucleotide position of the 5' base of the target or sense strand sequence relative to the human CSN5 mRNA sequence NM_006837. In certain embodiments, the sense and/or antisense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In some instances, the sense and/or antisense strand contains 3' overhangs comprising or consisting of DNA bases (e.g., "tt", "tg", or "tc") or RNA bases (e.g., "UU"). In other instances, the sense and/or antisense strand contains 3' overhangs that have complementarity to the target sequence or the complementary strand thereof. As a non-limiting example, the CSN5-2 sense strand (SEQ ID NO:3) and/or antisense strand (SEQ ID NO:4) may comprise or consist of a "tt" or "UU" 3' overhang.

Table 2 provides a list of chemically modified CSN5-2 siRNA containing 2'OMe nucleotides at selective positions within the double-stranded region.

TABLE 2

2'OMe-modified siRNA sequences that target human CSN5 gene expression.

| siRNA | Target or Sense Strand Sequence (5' → 3') | SEQ ID NO. | Antisense Strand Sequence (5' → 3') | SEQ ID NO. |
|---|---|---|---|---|
| CSN5-3/6 | GGA<u>U</u>CACCAU<u>U</u>AC<u>UUU</u>AAG | 27 | C<u>U</u>UAAAGUAAUGGUGA<u>U</u>CC | 28 |
| CSN5-3/7 | GGA<u>U</u>CACCAU<u>U</u>AC<u>UUU</u>AAG | 27 | C<u>UU</u>AAAGUAAU<u>GG</u>UGA<u>U</u>CC | 29 |
| CSN5-3/8 | GGA<u>U</u>CACCAU<u>U</u>AC<u>UUU</u>AAG | 27 | CUUAAA<u>G</u>UAAUG<u>GU</u>GA<u>U</u>CC | 30 |
| CSN5-3/9 | GGA<u>U</u>CACCAU<u>U</u>AC<u>UUU</u>AAG | 27 | CU<u>U</u>AAAGUAAUGG<u>U</u>GAUCC | 31 |
| CSN5-4/6 | <u>GG</u>AUCACCAUUACU<u>U</u>UA<u>AG</u> | 32 | C<u>U</u>UAAAGUAAUGGUGA<u>U</u>CC | 28 |
| CSN5-4/7 | <u>GG</u>AUCACCAUUACU<u>U</u>UA<u>AG</u> | 32 | C<u>UU</u>AAAGUAAU<u>GG</u>UGA<u>U</u>CC | 29 |
| CSN5-4/8 | <u>GG</u>AUCACCAUUACU<u>U</u>UA<u>AG</u> | 32 | CUUAAA<u>G</u>UAAUG<u>GU</u>GA<u>U</u>CC | 30 |
| CSN5-4/9 | <u>GG</u>AUCACCAUUACU<u>U</u>UA<u>AG</u> | 32 | CU<u>U</u>AAAGUAAUGG<u>U</u>GAUCC | 31 |
| CSN5-5/6 | G<u>GAU</u>CACCAUUACU<u>UU</u>AAG | 33 | C<u>U</u>UAAAGUAAUGGUGA<u>U</u>CC | 28 |
| CSN5-5/7 | G<u>GAU</u>CACCAUUACU<u>UU</u>AAG | 33 | C<u>UU</u>AAAGUAAU<u>GG</u>UGA<u>U</u>CC | 29 |
| CSN5-5/8 | G<u>GAU</u>CACCAUUACU<u>UU</u>AAG | 33 | CUUAAA<u>G</u>UAAUG<u>GU</u>GA<u>U</u>CC | 30 |
| CSN5-5/9 | G<u>GAU</u>CACCAUUACU<u>UU</u>AAG | 33 | CU<u>U</u>AAAGUAAUGG<u>U</u>GAUCC | 31 |

2'OMe nucleotides are indicated in bold and underlined in Table 2. The sense and/or antisense strand may alternatively or additionally comprise 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In some instances, the sense and/or antisense strand contains 3' overhangs comprising or consisting of DNA bases (e.g., "tt", "tg", or "tc") or RNA bases (e.g., "UU"). In other instances, the sense and/or antisense strand contains 3' overhangs that have complementarity to the target sequence or the complementary strand thereof. As a non-limiting example, the CSN5-3/8 sense strand (SEQ ID NO:27) and/or antisense strand (SEQ ID NO:30) may comprise or consist of a "tt" or "UU" 3' overhang.

Additional siRNA molecules targeting human CSN5 gene expression may comprise a sense strand (target) sequence comprising or consisting of 19-25 contiguous nucleotides of SEQ ID NO:34 and/or an antisense strand that is partially or completely complementary (e.g., at least about 80%, 85%, 90%, 95%, 96%, 97%, 98%, 99%, or 100% complementary) to the sense strand (target) sequence. Examples of such additional CSN5 siRNA sequences include, but are not limited to, nucleotides 1-19, 2-20, 3-21, 4-22, 5-23, 6-24, 7-25, 8-26, 9-27, 10-28, 11-29, 12-30, 13-31, 14-42, 15-33, 16-34, 17-35, 18-36, 19-37, 20-38, . . . , 450-468, 451-469, 452-470, 453-471, 454-472, 455-473, 456-474, 457-475, 458-476, 459-477, 460-478, 461-479, 462-480, 463-481, 464-482, 465-483, 466-484, 467-485, 468-486, 469-487, 470-488, 471-489, 472-490, 473-491, 474-492, 475-493, 476-494, 477-495, 478-496, 479-497, 480-498, 481-499, 482-500, 483-501, 484-502, 485-503, 486-504, 487-505, 488-506, 489-507, 490-508, 491-509, 492-510, 493-511, 494-512, 495-513, 496-514, 497-515, 498-516, 499-517, 500-518, . . . , 1485-1503, 1486-1504, 1487-1505, 1488-1506, 1489-1507, 1490-1508, 1491-1509, or 1492-1510 of SEQ ID NO:34. Either or both strands of the siRNA may comprise one or more modified nucleotides (e.g., 2'OMe nucleotides) and/or 3' overhangs as described herein.

Example 3 siRNA Targeting CSN5 Inhibit the Growth of Cancer Cells

Figure 1B:
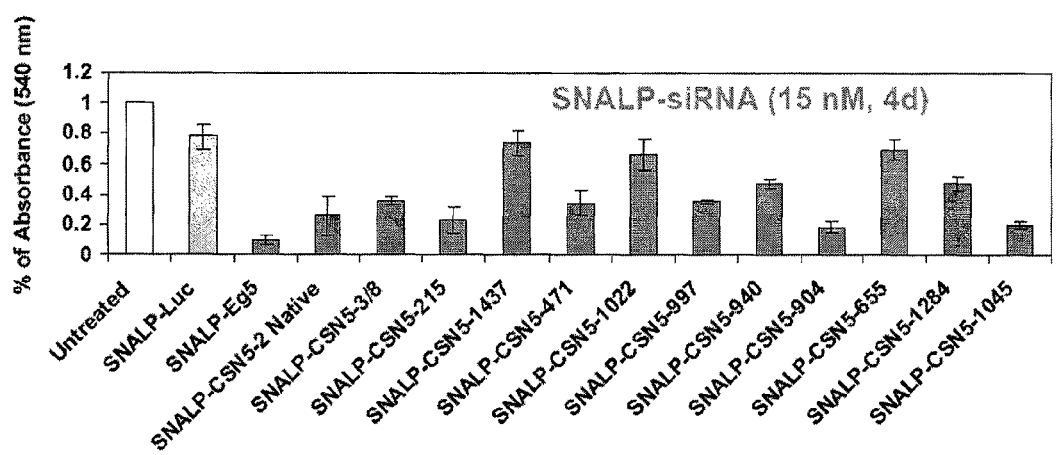
Figure 2A:
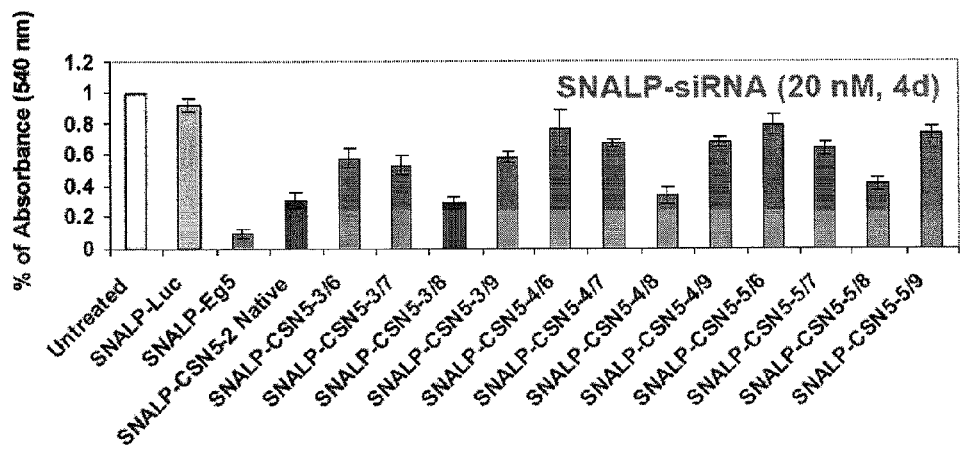
FIGS. 2A and 2B illustrate data demonstrating the effect of SNALP containing CSN5 siRNA on HepG2-1A1 cell growth. (A) Inhibition of HepG2-luc$^+$ cell growth after transfection with 20 nM of SNALP-formulated unmodified CSN5-2 siRNA or its modified variants. (B) Inhibition of HepG2-luc⁺ cell growth after transfection with 15 nM of SNALP-formulated siRNA targeting other regions of the CSN5 gene. The siRNA transfectants were examined by an MTT assay 4 d after the treatment. As controls, the cells that were untreated and treated with luciferase-specific siRNA were assayed simultaneously. Results are shown as the mean percentage of absorbance at 540 nm±s.d.
Figure 2B:
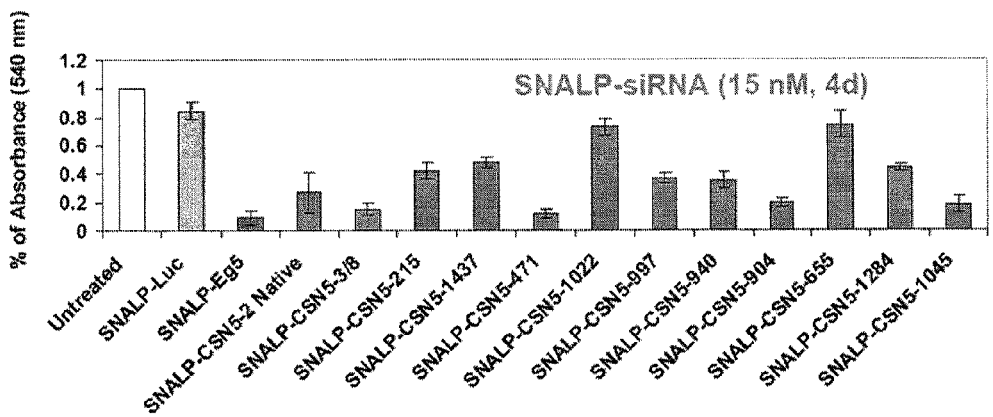

The CSN5 siRNA molecules set forth in Tables 1 and 2 above were formulated as SNALP (1:57 formulation: 1.4% PEG-cDMA; 57.1% DLinDMA; 7.1% DPPC; and 34.3% cholesterol) and evaluated for their inhibitory effects on cell growth in vitro. The human hepatocellular carcinoma (HCC) cell lines Huh7 or HepG2 were treated with CSN5 SNALP and their effect on cell viability was evaluated. Viability of cell cultures is expressed as % viability relative to PBS treated controls. FIGS. 1A (Huh7) and 2A (HepG2) show that SNALP containing 2'OMe-modified CSN5-2 siRNA were effective at inhibiting the growth of cells from both cell lines. In particular, SNALP containing either unmodified CSN5-2 siRNA or CSN5-3/8 siRNA were highly potent at killing Huh7 and HepG2 cells. The CSN5-3/8 siRNA was the most effective sequence and inhibited Huh7 cell growth by about 85%. FIGS. 1B (Huh7) and 2B (HepG2) show that SNALP containing siRNA targeting other regions of the CSN5 gene were also effective at inhibiting the growth of cells from both cell lines. SNALP containing Luciferase (Luc) siRNA was used as a negative control, and SNALP containing Eg5 siRNA was used as a positive control.

Example 4

Modified CSN5 siRNA Are Non-Immunostimulatory

The unmodified and 2'OMe-modified CSN5-2 siRNA molecules set forth in Tables 1 and 2 above were formulated as SNALP (1:57 formulation: 1.4% PEG-cDMA; 57.1% DLinDMA; 7.1% DPPC; and 34.3% cholesterol) and evaluated for their immunostimulatory activity in vitro. Flt3L DC cultures from mouse bone marrow were treated with CSN5 SNALP at 5 µg/ml for 24 hours. IL-6 levels in the culture supernatants were assayed as an indicator of immune stimulation by a particular CSN5 siRNA.

Figure 3:
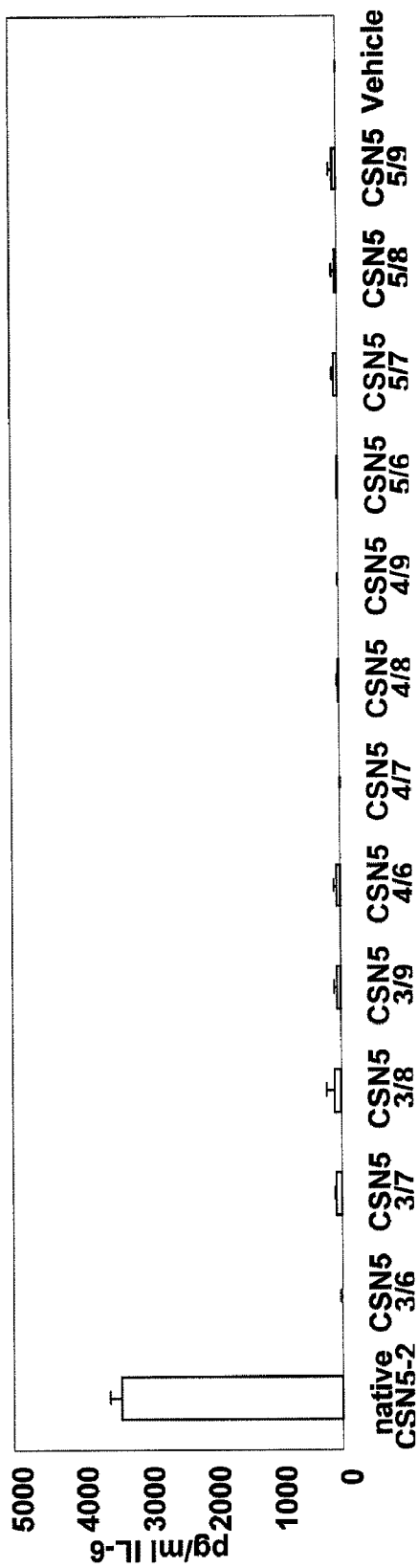
FIG. 3 illustrates data demonstrating that chemically modified CSN5-2 siRNA induced a minimal cytokine response in vitro. This figure shows the quantification of IL-6 levels after i.v. administration of SNALP-encapsulated unmodified or modified CSN5-2 siRNA into mice. After 24 h of siRNA treatment, culture supernatants of Flt3L-derived dendricytes isolated from mouse bone marrow were assayed for IL-6 by an ELISA method. Each value is the mean±s.d. of triplicate experiments.

FIG. 3 shows that SNALP containing unmodified (native) CSN5-2 siRNA induced high levels of IL-6 in murine Flt3L DC cultures, which was indicative of robust immune stimulation. However, 2'OMe-modified variants of CSN5-2 induced a minimal IL-6 response in this cell culture system. Furthermore, injection of empty particles did not induce significant IL-6 levels.

Example 5 siRNA Targeting CSN5 Affect the Course of HCC Progression

This example illustrates that (1) siRNA-mediated knockdown of CSN5 expression inhibited the proliferation of cells from both Huh7 and HepG2 cell lines; (2) treatment with siRNA targeting CSN5 increased apoptosis of HCC cells by restoring the protein levels of the p52 tumor suppressor and the p27 cdk inhibitor; (3) CSN5 silencing decreased the size of side population-containing cancer stem cells (CSC), indicating that targeting the CSN5 gene is effective in anti-CSC therapy; and (4) systemic delivery of SNALP containing chemically modified CSN5 siRNA effectively suppressed neoplastic growth in a mouse model of metastatic human liver cancer.

Silencing of CSN5 Inhibits the Proliferation and Cell Cycle Progression of Human HCC Cells Given the significance of p53 and p27 in hepatocarcinogenesis, the effects of CSN5 gene knockdown using human HCC cell lines were examined. To inactivate CSN5 gene, expression, Huh7 and HepG2 cells were treated with three different siRNA (CSN5-1, CSN5-2, and CSN5-3). The silencing of CSN5 gene expression was confirmed by quantitative real-time RT-PCR and Western blotting. Cell growth was then analyzed by MTT and FACS analysis, and apoptosis was estimated by ELISA for detection of ssDNA. In addition, flow cytometry was used to determine the size of side population (SP) defined by efflux of Hoechst 33342 dye and shown to be enriched in cancer stem cells as an approach to study the response of cancer stem cells to gene therapy.

FIG. 4 shows that CSN5 gene silencing decreased HCC cell survival in a cell viability assay and reduced CSN5 mRNA levels in a quantitative real-time RT-PCR assay. Among the siRNA tested, the CSN5-2 siRNA was the most effective in inhibiting HCC cell growth. Huh7 and HepG2 cells transfected with CSN5-2 siRNA for 4 days showed ~68% and ~77% growth inhibition, respectively (FIGS. 4A-B). In contrast, negative control (NC) siRNA revealed only marginal inhibition of Huh7 and HepG2 cell growth (i.e., less than 14% and 13% inhibition) at the same concentrations when compared to no treatment. Quantitative analysis of target mRNA was performed to test the effect of siRNA on CSN5 gene expression in both Huh7 and HepG2 cells. A 48 hour treatment with 15 nM CSN5-2 siRNA resulted in ~87% and ~90% reduction of target mRNA in Huh7 and HepG2 cells, respectively (FIGS. 4C-D).

Figure 5:
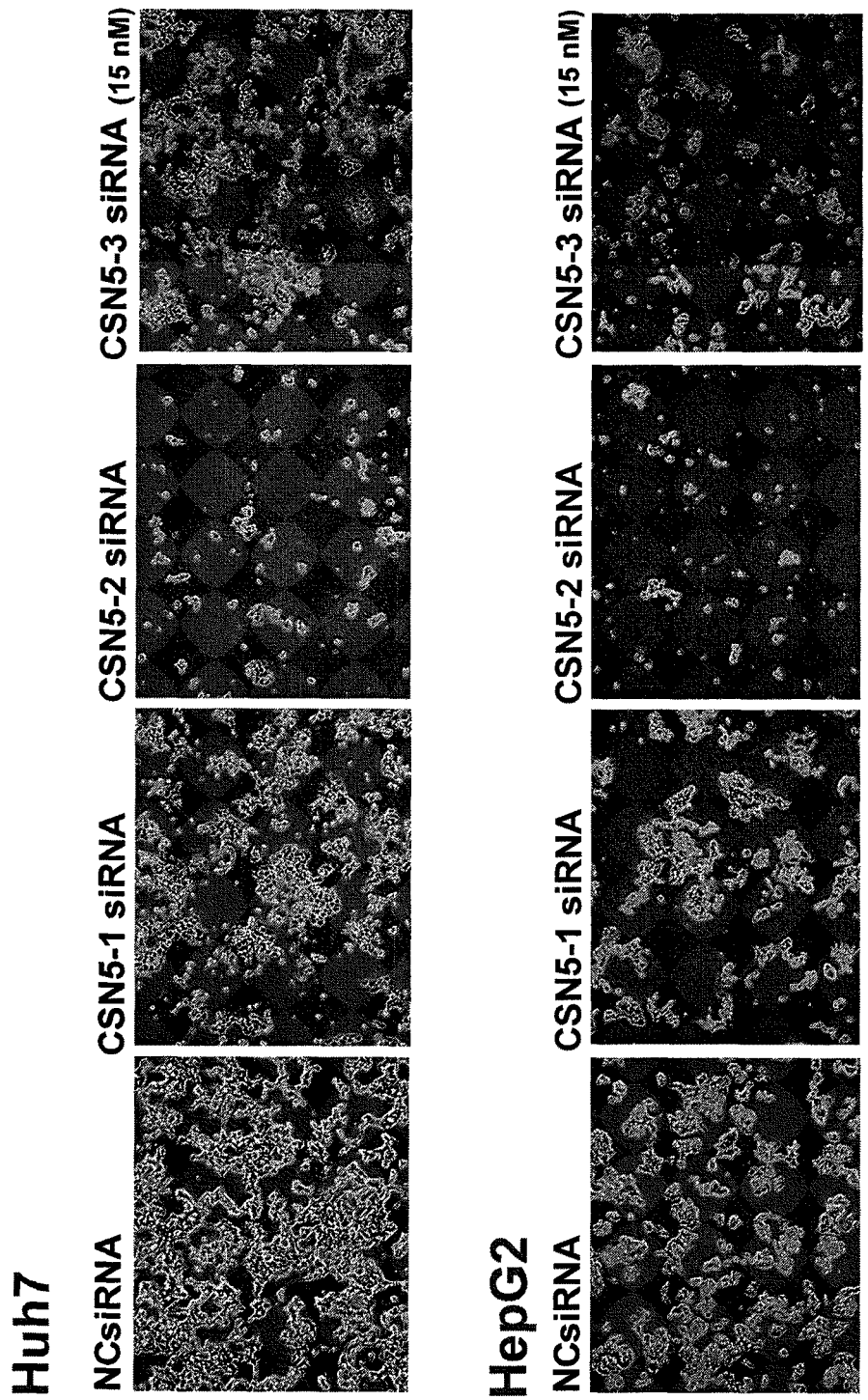
FIG. 5 illustrates data demonstrating that CSN5 gene silencing decreased HCC cell survival as detected by light microscopy. The effect of CSN5-specific siRNA on morphological changes was observed in Huh7 or HepG2 cells treated with 15 nM of the siRNA for 4 d (100× magnification).
Figure 7A:
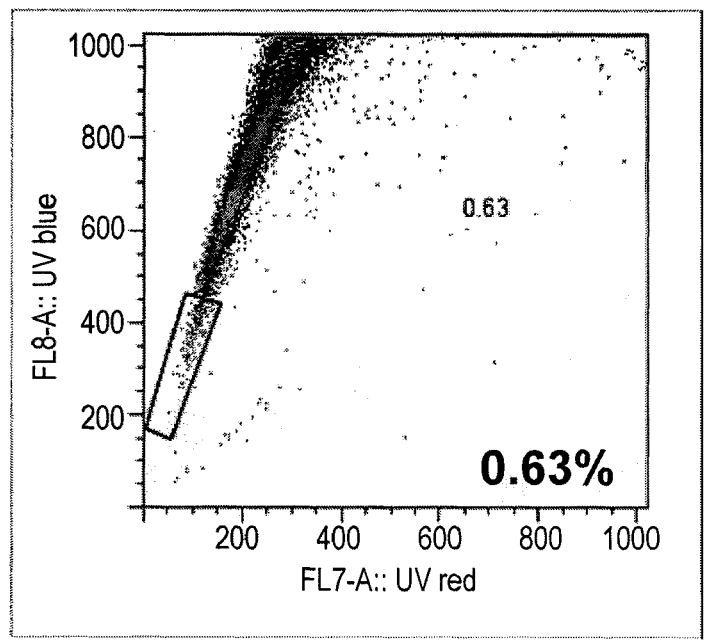
FIGS. 7A-7D illustrate data demonstrating that silencing of CSN5 expression was capable of reducing the proportion of side population (SP) cells. Changes in SP fraction after transfection of Huh7 or HepG2 cells with 15 nM of CSN5-2 siRNA for 48 h were analyzed. Flow cytometry was used to determine the size of SP defined by efflux of Hoechst 33342 dye and shown to be enriched in cancer stem cells. The cells that were treated with NCsiRNA were assayed simultaneously.
Figure 7B:
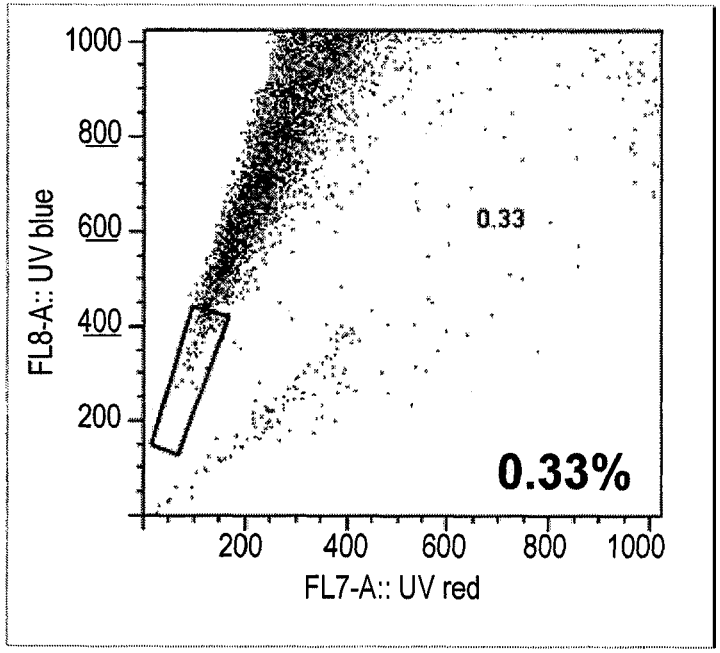
Figure 7C:
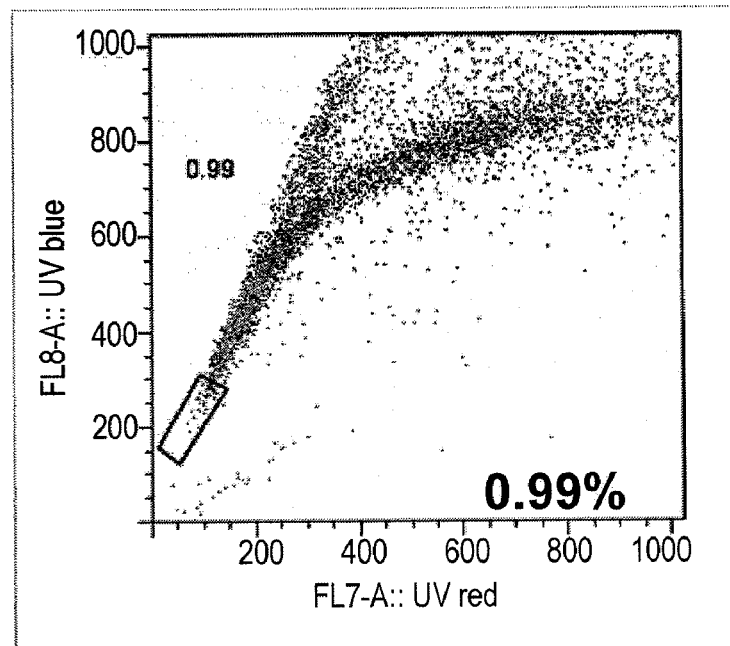
Figure 7D:
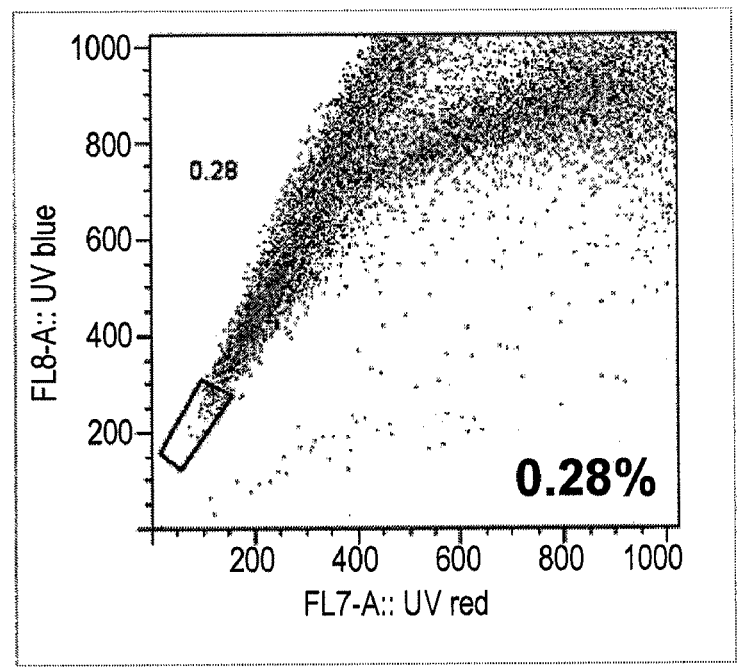

FIG. 5 shows that CSN5 gene silencing decreased HCC cell survival as detected by light microscopy. As such, the observed phenotypic changes in cell morphology confirmed the results of the cell proliferation assay.

FIG. 6 shows that CSN5 gene silencing is associated with cell cycle arrest in the G1 phase. In terms of the effect on cell cycle progression, compared to control treatments, target gene silencing by CSN5 siRNA generally increased the G0/G1 population with a compensatory decrease in G2/M phase of both Huh7 and HepG2 cells, ultimately inducing a cell cycle arrest in the G1 phase.

FIG. 7 shows that silencing of CSN5 gene expression was capable of reducing the proportion of side population (SP) cells (~50% and ~70% in Huh7 and HepG2, respectively), indicating that targeting of the CSN5 gene is effective in anticancer stem cell therapy. In particular, flow cytometry was used to determine the size of SP cells defined by the efflux of Hoechst 33342 dye and shown to be enriched in cancer stem cells as an approach to study the response of cancer stem cells to siRNA therapy.

These results demonstrate that siRNA-mediated knockdown of CSN5 blocks the proliferation and cell cycle progressions of human HCC cells and is an effective form of anti-cancer stem cell therapy.

Induction of Apoptosis by Functional Restoration of p53 Tumor Suppressor

Figure 8A:
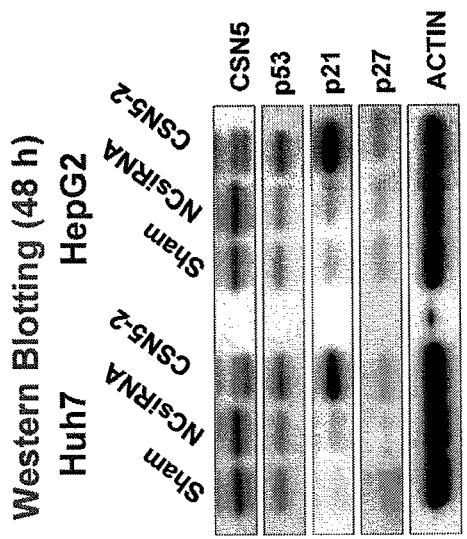
FIGS. 8A-8C illustrate data demonstrating that CSN5 gene silencing increased apoptosis by restoring p53 and p27 levels. (A, B) Detection of apoptotic progression in Huh7 (A) or HepG2 (B) cells 3 d after transfection with 15 nM of CSN5-2 siRNA. The cells that were untreated (sham) and treated with NCsiRNA were assayed simultaneously. Results are shown as the mean fold-induction of apoptosis±s.d. of three independent experiments. (C) Western blot analysis of CSN5, p53, p21, and p27 protein expression in Huh7 or HepG2 cells that were untreated (Sham) or treated with 15 nM of NCsiRNA or CSN5-2 siRNA for 48 h.
Figure 8B:
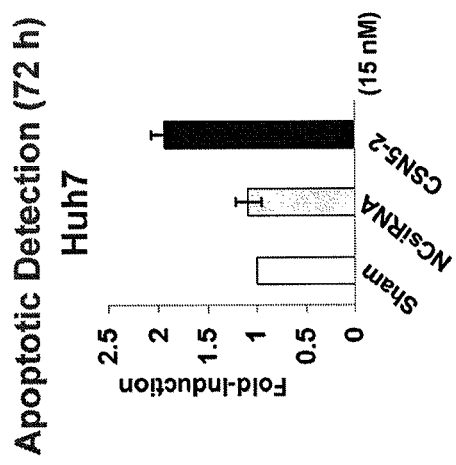

This study analyzed whether the cancer cell death caused by CSN5 siRNA treatment reflected the induction of apoptosis. Huh7 and HepG2 cells treated with 15 nM of CSN5-2 siRNA for 3 days were subjected to an assay that detects denatured DNA within cells, which is an indicator of the changes in chromatin associated with apoptotic progression. CSN5-deficient Huh7 and HepG2 cells exhibited ~1.8-fold increase in apoptosis as compared with negative control (NC) siRNA-treated cells, a property which was directly correlated with the extent of downregulation of CSN5 mRNA levels (FIGS. 8A-B).

Figure 8C:
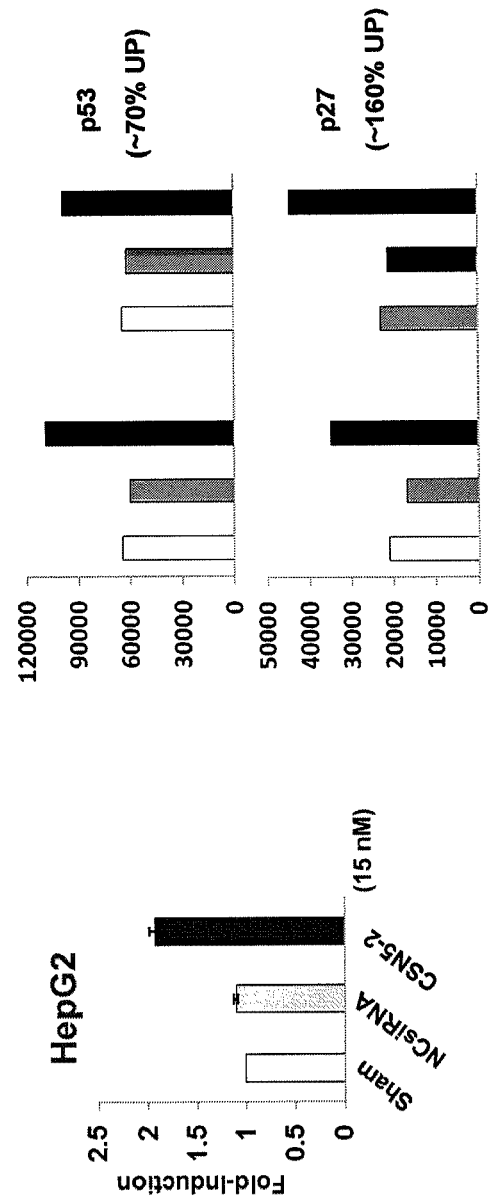

Furthermore, the levels of p53, its responder p21, and p27 were restored when HCC cells were undergoing apoptotic progression through downregulation of CSN5 protein by siRNA treatment. In particular, when HCC cells were undergoing apoptotic progression through the downregulation of CSN5 protein, the level of intracellular total p53 protein was increased by about 2-fold as compared to treatment with an equal amount of NCsiRNA (FIG. 8C). Similar to the elevation of p53 levels, cellular p21 levels increased by about 9.3-fold and 13.7-fold in Huh7 and HepG2 cells, respectively, and p27 levels increased as well (~1.6 fold). These results indicate that the growth inhibition of HCC cells by CSN5 siRNA is mediated by apoptotic induction that is triggered by functional restoration of the p53 tumor suppressor.

Figure 9A:
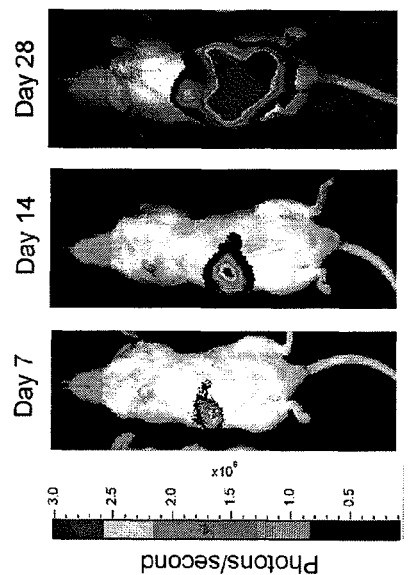
FIGS. 9A and 9B illustrate data demonstrating the establishment of an Huh7-luc⁺ orthotopic liver transplantation (OLT) model. This figure shows the stable expression of luciferase in Huh7 cells and transplantation of Huh7-luc⁺ cells into the spleen of immunodeficient mice. (A) Screening of clones that are stably expressing luciferase by in vitro BLI. Cells were diluted to 5,000 or 10,000, plated in four wells, and imaged for 10 sec after the addition of luciferin (150 µg/ml final) to media. (B) In vivo analysis of tumor cell liver colonization. $5 \times 10^5$ Huh7-luc⁺ cells were transplanted into spleen of SCID-beige mice, and tumor growth in liver was assessed by whole mouse BLI with a regular interval.
Figure 9B:
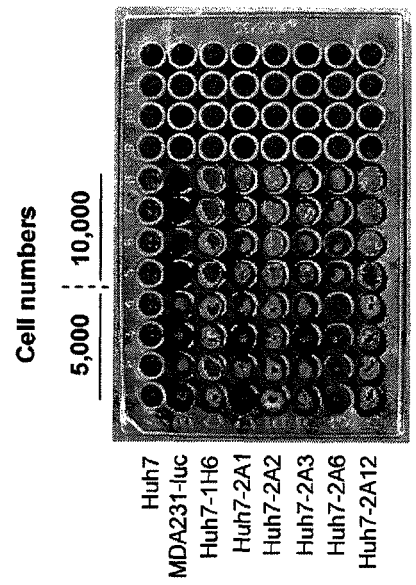

Construction of In Vivo Evaluation Model with Systemic Silencing of the CSN5 Gene For systemic validation of therapeutic targets using siRNA, it is essential to establish an HCC mouse model, a stable system for siRNA delivery to target tissue, and persistent monitoring of tumor response after treatment. Recently, a new in vivo molecular imaging method to detect tumors in animals has emerged based on visible light emission from luciferase-expressing cells or tissues (Contag et al., NeoRev., 1:e225-232 (2000)). Therefore, bioluminescent human HCC cells which constitutively express luciferase were established for both the development of HCC orthotopic xenograft models and detection of their response by target siRNA administration. The β-actin promoter was subcloned upstream of the luciferase gene in the pGL4.17 reporter vector to enhance its expression within cells, and then transfected into Huh7 cells. Among the numerous foci grown under the condition of antibiotic selection, the Huh7-1H6 clone that had a highest level of luciferase expression was selected (FIG. 9A) and named Huh7-luc$^+$ cells. About half a million bioluminescent Huh7 cells permanently expressing luciferase were transplanted into the spleen of immunodeficient SCID-beige mice to establish an Huh7-luc$^+$ HCC orthotopic xenograft model for in vivo evaluation of CSN5 as a therapeutic target. Right after the cell injection, spleens were removed. Tumors were detectable from day 7 by bioluminescence imaging (BLI), and kept growing exponentially up to day 28 (FIG. 9B).

Systemic Inhibition of Orthotopic Liver Tumor Growth

Eight days after transplantation of Huh7-luc$^+$ cells, SNALP (1:57 formulation: 1.4% PEG-cDMA; 57.1% DLinDMA; 7.1% DPPC; and 34.3% cholesterol) containing CSN5-3/8 siRNA were systemically delivered to the liver through a tail vein injection four times (days 8, 11, 14, and 18) at a dosage of 2 mg/kg. Tumor relapses were monitored by bioluminescence imaging (BLI) up to 28 days after cell transplantation.

Figure 10A:
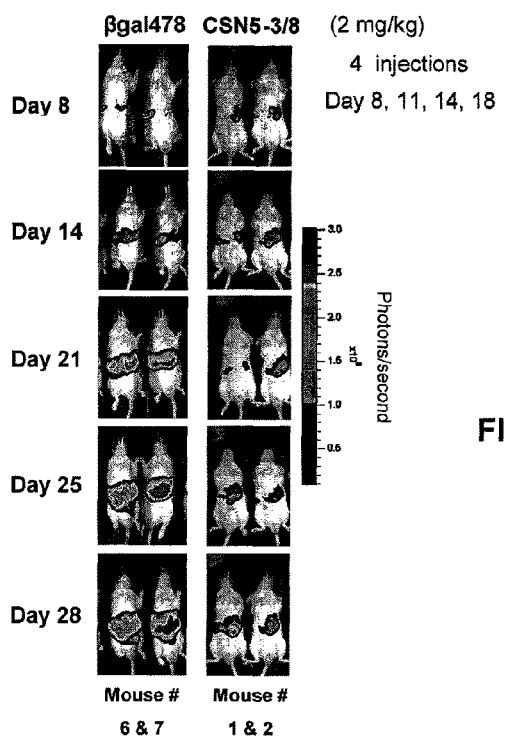
FIGS. 10A-10D illustrate data demonstrating that treatment with SNALP containing CSN5-3/8 siRNA effectively suppressed neoplastic growth in a mouse model of metastatic human liver cancer. In particular, this figure shows that the systemic targeting of CSN5 by SNALP-formulated CSN5-3/8 siRNA suppressed Huh7-luc⁺ orthotopic tumor growth in the liver. (A) In vivo monitoring of tumor growth by BLI during and after treatments. Images of two representative mice from each treatment group are shown. On days 8, 11, 14, and 18 after transplantation, SNALP-formulated βgal478 or CSN5 3/8 siRNA was injected into the tail vein with a dosage of 2 mg/kg. Images were set at the same pseudocolor scale to show relative bioluminescent changes over time. (B) Measurement of mean in vivo tumor bioluminescence. Bioluminescent signals emitted from the liver tumors of Huh7-luc⁺ cells were quantified in photons/second at each imaging time point, and mean tumor bioluminescence±s.d. was graphed over time for the mice treated with SNALP-formulated βgal478 or CSN5 3/8 siRNA. (C) This panel shows examples of the gross liver morphology of excised livers on day 28 after administration of SNALP-formulated βgal478 or CSN5 3/8 siRNA. (D) This panel shows the gross liver morphology and histological analysis of excised livers on day 28 after administration of SNALP-formulated βgal478 or CSN5 3/8 siRNA. Livers from all mice tested were sectioned and stained with H&E to observe the status of tumor growth within tissues. Both gross liver morphology and a microscopic image (100×) of a representative liver from each treatment group are shown.
Figure 10B:
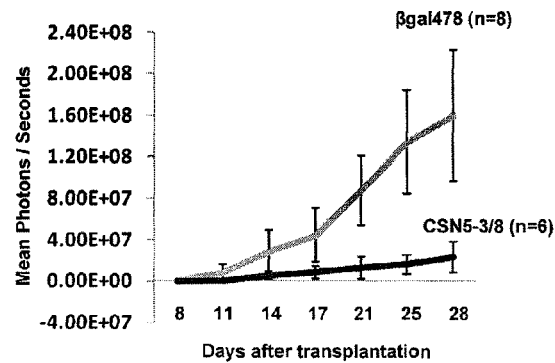
Figure 10C:
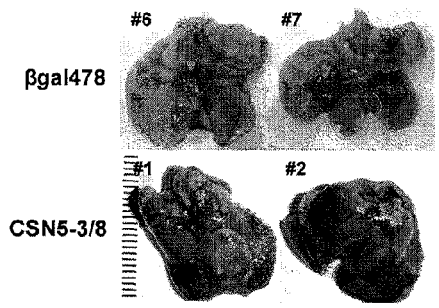
Figure 10D:
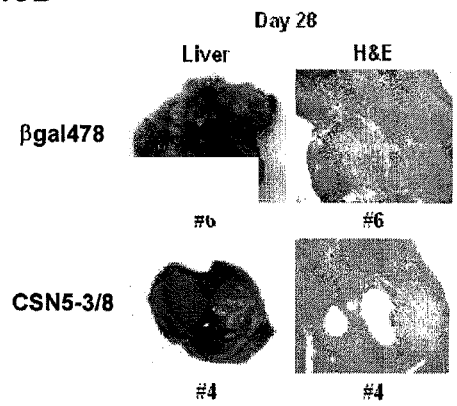

Compared to a control administration of SNALP containing siRNA targeting β-galactosidase, systemic delivery of CSN5-3/8 siRNA effectively prevented orthotopic tumor growth in the liver in a mouse model of metastatic human liver cancer (FIGS. 10A-B). Correlating with the level of bioluminescent signals on day 28, gross inspection revealed that the livers in mice treated with CSN5-3/8 siRNA had a significantly lower number of tumors or a complete absence of tumors (FIGS. 10C-D). Histological analysis also revealed that livers treated with control siRNA produced tumors, indicating a significant degree of cellular proliferation. In contrast, CSN5-3/8 siRNA treatment inhibited tumor spreading, even at the modest dose.

Figure 11:
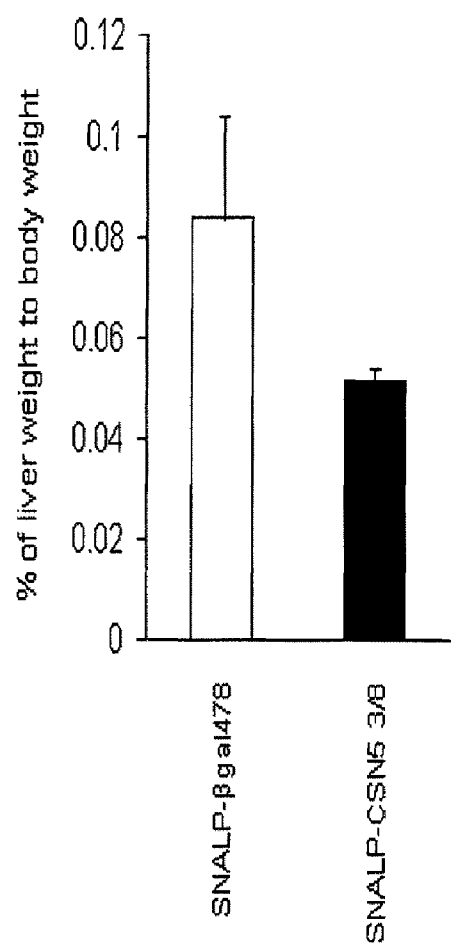
FIG. 11 illustrates data demonstrating that liver to body weight ratios were lower in SNALP-formulated CSN5 3/8 siRNA-treated versus SNALP-formulated βgal478 siRNA-treated (control) mice. In particular, liver to body weight ratios of mice that were treated four times with 2 mg/kg of SNALP-formulated βgal478 or CSN5 3/8 siRNA are shown. Each bar represents the mean ratio of liver:body weight±s.d. from each treatment group.

Liver to body weight ratios were also lower in CSN5-3/8 siRNA-treated versus control siRNA-treated mice, further confirming tumor growth suppression (FIG. 11).

These results demonstrate that CSN5 is an important regulator of HCC cell growth and survival, and p53 ubiquitination represents a target pathway for human HCC treatment.

Conclusion

Accordingly, this example demonstrates that the potency of systemic delivery of siRNA targeting CSN5 without overt toxicity is a clinically viable therapeutic modality for the treatment of liver cancers such as HCC. In particular, this example illustrates that CSN5 is an important regulator of HCC cell growth and survival, and is an attractive target for HCC therapy. Importantly, this example shows that SNALP containing siRNA targeting CSN5 gene expression are efficacious for the in vivo delivery and treatment of liver cancers such as HCC.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. An siRNA molecule for silencing COP9 signalsome subunit 5 (CSN5) gene expression comprising a double-stranded region of 19 to about 25 nucleotides in length, wherein the siRNA molecule comprises a sense strand sequence comprising SEQ ID NO:17 and an antisense strand sequence comprising SEQ ID NO:18.

2. The siRNA molecule of claim 1, wherein one or more of the nucleotides in the double-stranded region comprise modified nucleotides.

3. The siRNA molecule of claim 2, wherein the modified nucleotides comprise 2'-O-methyl (2'OMe) nucleotides.

4. A nucleic acid-lipid particle comprising:
(a) an siRNA molecule of claim 1;
(b) a cationic lipid; and
(c) a non-cationic lipid.

5. The nucleic acid-lipid particle of claim 4, wherein the cationic lipid comprises from about 50 mol % to about 85 mol % of the total lipid present in the particle.

6. The nucleic acid-lipid particle of claim 4, wherein the non-cationic lipid comprises a mixture of a phospholipid and cholesterol or a derivative thereof.

7. The nucleic acid-lipid particle of claim 6, wherein the phospholipid comprises from about 4 mol % to about 10 mol % of the total lipid present in the particle and the cholesterol comprises from about 30 mol % to about 40 mol % of the total lipid present in the particle.

8. The nucleic acid-lipid particle of claim 4, wherein the non-cationic lipid comprises cholesterol or a derivative thereof.

9. The nucleic acid-lipid particle of claim 4, further comprising a conjugated lipid that inhibits aggregation of particles.

10. A method for introducing an siRNA that silences CSN5 gene expression into a cell, the method comprising:
contacting the cell with an siRNA molecule of claim 1.

11. A method for the in vivo delivery of an siRNA that silences CSN5 gene expression, the method comprising:
administering to a mammalian subject an siRNA molecule of claim 1.

12. A method for treating cancer in a mammalian subject in need thereof, the method comprising:
administering to the mammalian subject a therapeutically effective amount of an siRNA molecule of claim 1.

13. The siRNA molecule of claim 1, wherein the siRNA molecule comprises a 3' overhang in one or both strands of the siRNA molecule.

14. The siRNA molecule of claim 2, wherein from about 15% to about 30% of the nucleotides in the double-stranded region comprise modified nucleotides.

15. The siRNA molecule of claim 3, wherein the 2'OMe nucleotides are selected from the group consisting of 2'OMe-guanosine nucleotides, 2'OMe-uridine nucleotides, 2'OMe-adenosine nucleotides, 2'OMe-cytosine nucleotides, and mixtures thereof.

16. The siRNA molecule of claim 3, wherein the siRNA molecule comprises at least one 2'OMe-guanosine nucleotide and at least one 2'OMe-uridine nucleotide.

17. The siRNA molecule of claim 2, wherein the modified nucleotides are present in one or both strands of the siRNA molecule.

18. A pharmaceutical composition comprising an siRNA molecule of claim 1 and a pharmaceutically acceptable carrier.

19. The nucleic acid-lipid particle of claim 9, wherein the conjugated lipid that inhibits aggregation of particles comprises a polyethyleneglycol (PEG)-lipid conjugate.

20. A pharmaceutical composition comprising a nucleic acid-lipid particle of claim 4 and a pharmaceutically acceptable carrier.

* * * * *